(12) United States Patent
Berme et al.

(10) Patent No.: US 12,013,542 B1
(45) Date of Patent: Jun. 18, 2024

(54) HEAD-MOUNTED DISPLAY SYSTEM

(71) Applicant: Bertec Corporation, Columbus, OH (US)

(72) Inventors: Necip Berme, Worthington, OH (US); Murat Kerim Berme, Venice, CA (US); Mohan Chandra Baro, Columbus, OH (US); Megan Elaine Cotterman, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 18/389,191

(22) Filed: Nov. 13, 2023

Related U.S. Application Data

(63) Continuation-in-part of application No. 17/965,745, filed on Oct. 13, 2022, now Pat. No. 11,816,258.

(51) Int. Cl.
*A61B 3/113* (2006.01)
*A61B 3/00* (2006.01)
(Continued)

(52) U.S. Cl.
CPC ..... *G02B 27/0172* (2013.01); *G02B 27/0093* (2013.01); *G06F 3/012* (2013.01); *G06F 3/016* (2013.01); *G06F 3/0334* (2013.01); *G06F 3/0338* (2013.01); *G06T 19/006* (2013.01); *G02B 2027/0112* (2013.01); *G02B 2027/0138* (2013.01); *G02B 2027/014* (2013.01); *G06F 2203/0382* (2013.01)

(58) Field of Classification Search
CPC ... A61B 3/0008; A61B 3/0025; A61B 3/0033; A61B 3/0041; A61B 3/113; A61B 3/145; A61B 3/18; A61B 5/1036; A61B 5/4023; A61B 5/486; G02B 27/0093; G06F 3/011; G06F 3/013; G06T 15/00
See application file for complete search history.

(56) References Cited

U.S. PATENT DOCUMENTS

| 6,038,488 A | 3/2000 | Barnes et al. |
| 6,113,237 A | 9/2000 | Ober et al. |

(Continued)

OTHER PUBLICATIONS

Notice of Allowance in U.S. Appl. No. 17/965,745, dated Jul. 10, 2023.

*Primary Examiner* — Jack Dinh
(74) *Attorney, Agent, or Firm* — The Law Office of Patrick F. O'Reilly III, LLC

(57) ABSTRACT

A head-mounted display system is disclosed herein. In one or more embodiments, the head-mounted display system includes a head-mounted visual display device and an instrumented floor with one or more instrumented floor sections configured to detect movements, forces, and/or moments for a user and generate one or more output signals based upon the detected movements, forces, and/or moments for the user; and at least one data processing device operatively coupled to the head-mounted visual display device and the instrumented floor. The at least one data processing device being programmed to receive the one or more output signals from the instrumented floor; and determine one or more movements, output forces, and/or output moments for the user based upon the one or more output signals from the instrumented floor. The instrumented floor enables a plurality of different movement patterns and/or protocols to be executed thereon by the user.

11 Claims, 13 Drawing Sheets

(51) Int. Cl.
*G02B 27/00* (2006.01)
*G02B 27/01* (2006.01)
*G06F 3/01* (2006.01)
*G06F 3/033* (2013.01)
*G06F 3/0338* (2013.01)
*G06T 15/00* (2011.01)
*G06T 19/00* (2011.01)

(56) References Cited

U.S. PATENT DOCUMENTS

| | | | |
|---|---|---|---|
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,936,016 B2 | 8/2005 | Berme et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 9,916,011 B1 | 3/2018 | Berme et al. | |
| 9,927,312 B1 | 3/2018 | Berme et al. | |
| 10,010,248 B1 | 7/2018 | Shearer | |
| 10,010,286 B1 | 7/2018 | Berme et al. | |
| 10,085,676 B1 | 10/2018 | Berme et al. | |
| 10,117,602 B1 | 11/2018 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,264,964 B1 | 4/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,463,250 B1 | 11/2019 | Berme et al. | |
| 10,527,508 B2 | 1/2020 | Berme et al. | |
| 10,555,688 B1 | 2/2020 | Berme et al. | |
| 10,646,153 B1 | 5/2020 | Berme et al. | |
| 10,722,114 B1 | 7/2020 | Berme et al. | |
| 10,736,545 B1 | 8/2020 | Berme et al. | |
| 10,765,936 B2 | 9/2020 | Berme et al. | |
| 10,803,990 B1 | 10/2020 | Wilson et al. | |
| 10,853,970 B1 | 12/2020 | Akbas et al. | |
| 10,856,796 B1 | 12/2020 | Berme et al. | |
| 10,860,843 B1 | 12/2020 | Berme et al. | |
| 10,945,599 B1 | 3/2021 | Berme et al. | |
| 10,966,606 B1 | 4/2021 | Berme | |
| 11,033,453 B1 | 6/2021 | Berme et al. | |
| 11,052,288 B1 | 7/2021 | Berme et al. | |
| 11,054,325 B2 | 7/2021 | Berme et al. | |
| 11,074,711 B1 | 7/2021 | Akbas et al. | |
| 11,097,154 B1 | 8/2021 | Berme et al. | |
| 11,158,422 B1 | 10/2021 | Wilson et al. | |
| 11,182,924 B1 | 11/2021 | Akbas et al. | |
| 11,262,231 B1 | 3/2022 | Berme et al. | |
| 11,262,258 B2 | 3/2022 | Berme et al. | |
| 11,301,045 B1 | 4/2022 | Berme et al. | |
| 11,311,209 B1 | 4/2022 | Berme et al. | |
| 11,321,868 B1 | 5/2022 | Akbas et al. | |
| 11,337,606 B1 | 5/2022 | Berme et al. | |
| 11,348,279 B1 | 5/2022 | Akbas et al. | |
| 11,458,362 B1 | 10/2022 | Berme et al. | |
| 11,521,373 B1 | 12/2022 | Akbas et al. | |
| 11,540,744 B1 | 1/2023 | Berme | |
| 11,604,106 B2 | 3/2023 | Berme et al. | |
| 11,631,193 B1 | 4/2023 | Akbas et al. | |
| 11,688,139 B1 | 6/2023 | Karagoz et al. | |
| 11,705,244 B1 | 7/2023 | Berme | |
| 11,712,162 B1 | 8/2023 | Berme et al. | |
| 11,790,536 B1 | 10/2023 | Berme et al. | |
| 11,798,182 B1 | 10/2023 | Karagoz et al. | |
| 11,816,258 B1 | 11/2023 | Berme et al. | |
| 11,826,601 B1 | 11/2023 | Berme | |
| 11,850,078 B1 | 12/2023 | Berme | |
| 11,857,331 B1 | 1/2024 | Berme et al. | |
| 11,865,407 B1 | 1/2024 | Berme et al. | |
| 2003/0216656 A1 | 11/2003 | Berme et al. | |
| 2008/0228110 A1 | 9/2008 | Berme | |
| 2011/0277562 A1 | 11/2011 | Berme | |
| 2012/0266648 A1 | 10/2012 | Berme et al. | |
| 2012/0271565 A1 | 10/2012 | Berme et al. | |
| 2015/0096387 A1 | 4/2015 | Berme et al. | |
| 2016/0245711 A1 | 8/2016 | Berme et al. | |
| 2016/0334288 A1 | 11/2016 | Berme et al. | |
| 2018/0024015 A1 | 1/2018 | Berme et al. | |
| 2019/0078951 A1 | 3/2019 | Berme et al. | |
| 2020/0139229 A1 | 5/2020 | Berme et al. | |
| 2020/0408625 A1 | 12/2020 | Berme et al. | |
| 2021/0333163 A1 | 10/2021 | Berme et al. | |
| 2022/0178775 A1 | 6/2022 | Berme et al. | |

HEAD-MOUNTED DISPLAY SYSTEM

CROSS-REFERENCE TO RELATED APPLICATIONS

This is a continuation-in-part of U.S. patent application Ser. No. 17/965,745, entitled "Head-Mounted Display System", filed on Oct. 13, 2022, the disclosure of which is hereby incorporated by reference as if set forth its entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a head-mounted display system. More particularly, the invention relates to a head-mounted display system configured to be used for balance testing and training.

2. Background

Measurement and testing systems are utilized in various fields to detect and analyze many different measurable quantities. For example, in biomedical applications, measurement and testing systems are used for gait analysis, assessing balance and mobility, evaluating sports performance, and assessing ergonomics. However, conventional measurement and testing systems have numerous limitations and drawbacks.

For example, conventional measurement and testing systems with large measurement surface areas and large visual displays are complex, difficult to install, and are not easily adaptable to different space configurations in a building. Also, these conventional measurement and testing systems are typically cost prohibitive for small clinical applications.

What is needed, therefore, is a head-mounted display system for assessing balance and mobility. Moreover, a head-mounted display system is needed for enhancing the visual motor performance of individuals. Furthermore, a need exists for a head-mounted display system as part of the rehabilitation regime for an orthopedic and/or neurological injury.

BRIEF SUMMARY OF EMBODIMENTS OF THE INVENTION

Accordingly, the present invention is directed to a head-mounted display system that substantially obviates one or more problems resulting from the limitations and deficiencies of the related art.

In accordance with one or more other embodiments of the present invention, there is provided a head-mounted display system that includes an input device, the input device configured to output an input signal based upon an input response by the user; a head-mounted visual display device having an output screen, the head-mounted visual display device configured to display one or more screen images on the output screen so that the one or more screen images are viewable by the user; and at least one data processing device, the at least one data processing device operatively coupled to the input device and the head-mounted visual display device. The at least one data processing device being programmed to: (i) generate and display at least one visual target on the output screen of the head-mounted visual display device; (ii) receive an input signal from the input device based upon an input response by the user; (iii) determine an orientation angle of a body portion of the user based upon the input signal received from the input device; and (iv) determine how closely the orientation angle of the body portion of the user corresponds to a tilt of the at least one visual target on the output screen of the head-mounted visual display device.

In a further embodiment of the present invention, the input device comprises a head position sensing device and the input signal comprises one or more measurement signals outputted by the head position sensing device, the one or more measurement signals being generated based upon a head movement of the user, and the orientation angle of the body portion of the user comprises a head angle of the user based upon the one or more measurement signals outputted by the head position sensing device.

In yet a further embodiment, the head-mounted visual display device comprises the head position sensing device.

In accordance with one or more other embodiments of the present invention, there is provided a head-mounted display system that includes a head-mounted visual display device having an output screen, the head-mounted visual display device configured to display one or more screen images on the output screen so that the one or more screen images are viewable by a user; an instrumented floor, the instrumented floor comprising one or more instrumented floor sections, the one or more instrumented floor sections configured to detect movements, forces, and/or moments for the user and generate one or more output signals based upon the detected movements, forces, and/or moments for the user; and at least one data processing device, the at least one data processing device operatively coupled to the head-mounted visual display device and the instrumented floor. The at least one data processing device being programmed to: (i) receive the one or more output signals from the instrumented floor; and (ii) determine one or more movements, output forces, and/or output moments for the user based upon the one or more output signals from the instrumented floor. In these one or more embodiments, the instrumented floor enables a plurality of different movement patterns and/or protocols to be executed by the user while the user is disposed on the instrumented floor.

In a further embodiment of the present invention, the one or more instrumented floor sections comprise one or more force measurement assemblies, the one or more force measurement assemblies configured to detect one or more forces and/or one or more moments for the user and generate the one or more output signals based upon the detected one or more forces and/or one or more moments for the user.

In yet a further embodiment, the one or more force measurement assemblies comprise a plurality of force measurement assemblies forming the instrumented floor, the one or more output signals comprise a plurality of output signals outputted by the plurality of force measurement assemblies, and the at least one data processing device is further programmed to: (iii) in a first operational mode, determine the output forces and/or output moments separately for at least some of the plurality of force measurement assemblies forming the instrumented floor; and (iv) in a second operational mode, determine the output forces and/or output moments for individual ones of the plurality of force measurement assemblies, and then combine the output forces and/or output moments for at least some of the plurality of force measurement assemblies so as to form a virtual force measurement assembly.

In still a further embodiment, the at least one data processing device is further programmed to: (iii) determine the one or more output forces and/or output moments for the user from the one or more output signals from the one or more force measurement assemblies; and (iv) determine performance metrics for the user based upon the one or more output forces and/or output moments.

In yet a further embodiment, the head-mounted visual display device further comprises a head position and/or movement sensing device operatively coupled to the at least one data processing device, the head position and/or movement sensing device configured to detect at least one of head position, head movement, head orientation, head velocity, and head acceleration of the user, and the at least one data processing device is further programmed to: (iii) determine the one or more output forces and/or output moments for the user from the one or more output signals from the one or more force measurement assemblies; (iv) determine the at least one of the head position, the head movement, the head orientation, the head velocity, and the head acceleration of the user from the head position and/or movement sensing device; and (v) assess balance and/or body stability for the user based upon both the one or more output forces and/or output moments from the one or more force measurement assemblies and the at least one of the head position, the head movement, the head orientation, the head velocity, and the head acceleration of the user from the head position and/or movement sensing device.

In still a further embodiment, a plurality of different users and/or objects are disposed on the instrumented floor, and the at least one data processing device is further programmed to: (iii) determine positions and/or movements for the plurality of different users and/or objects disposed on the instrumented floor using the one or more output signals.

In yet a further embodiment, the at least one data processing device is further programmed to: (iii) generate at least one of visual feedback, auditory feedback, and/or tactile feedback for the user based upon the one or more output signals from the instrumented floor.

In still a further embodiment, the at least one data processing device is further programmed to: (iv) generate the visual feedback for the user based upon the one or more output signals from the instrumented floor by displaying one or more virtual objects to the user using the head-mounted visual display device.

In yet a further embodiment, the instrumented floor comprises one or more vibratory devices for providing the tactile feedback for the user, and wherein the at least one data processing device is further programmed to: (iv) generate the tactile feedback for the user based upon the one or more output signals from the instrumented floor by generating one or more tactile sensations for the user using the one or more vibratory devices.

In still a further embodiment, the at least one data processing device is further programmed to: (iii) determine locations for one or more objects or persons based upon the one or more output signals from the instrumented floor; and (iv) depict, using the head-mounted visual display device, the one or more objects or persons in a virtual reality environment or augmented reality environment based upon the locations determined from the one or more output signals from the instrumented floor.

In yet a further embodiment, the at least one data processing device is further programmed to: (iii) generate one or more virtual terrains, virtual obstacles, and/or virtual people on the output screen of the head-mounted visual display device so that the user is able to interact with the one or more virtual terrains, virtual obstacles, and/or virtual people in a virtual reality environment; and (iv) determine a performance of the user in the virtual reality environment with the one or more virtual terrains, virtual obstacles, and/or virtual people based upon the one or more output signals from the instrumented floor.

In accordance with yet one or more other embodiments of the present invention, there is provided a head-mounted display system that includes an input device, the input device configured to output an input signal based upon an input response by a user; a head-mounted visual display device having an output screen, the head-mounted visual display device configured to display one or more images on the output screen so that the one or more images are viewable by the user; at least one camera for enabling the user to see one or more images of a real-world environment outside of the head-mounted visual display device, the at least one camera configured to capture the one or more images of the real-world environment outside of the head-mounted visual display device; and at least one data processing device, the at least one data processing device operatively coupled to the input device and the head-mounted visual display device. The at least one data processing device being programmed to: (i) generate augmented digital content; (ii) receive an input signal from the input device based upon an input response by the user; and (iii) in response to the input signal from the input device, display at least a portion of the one or more images of the real-world environment captured by the at least one camera on the output screen of the head-mounted visual display device, and overlay the augmented digital content over the one or more images of the real-world environment so that the user is able to quickly check his or her surroundings without removing the head-mounted visual display device from his or her head.

In a further embodiment of the present invention, the at least one data processing device is further programmed to: (iv) receive a defined area within the real-world environment from the user that establishes one or more boundaries of the real-world environment; and (v) display the one or more boundaries of the real-world environment within a virtual reality environment or an augmented reality environment so as to prevent the user from colliding with one or more objects in the real-world environment.

In yet a further embodiment, the at least one data processing device is further programmed to: (iv) manipulate the augmented digital content such that the augmented digital content interacts with one or more actual objects in the real-world environment.

In still a further embodiment, the at least one data processing device is further programmed to: (iv) overlay instructions or data over the one or more images of the real-world environment so that the user is able to receive guidance as to how to interact with the real-world environment.

In yet a further embodiment, the at least one data processing device is further programmed to: (iv) capture one or more hand movements of the user in the real-world environment using the at least one camera; and (v) enable the user to interact with one or more virtual elements using the one or more hand movements of the user captured from the real-world environment.

In still a further embodiment, the at least one data processing device is further programmed to: (iv) perform object recognition on the one or more images of the real-world environment captured by the at least one camera so as to identify one or more real-world objects; and (v) generate the augmented digital content based upon the one or more real-world objects identified in the real-world environment so as to provide a context-aware augmented reality experience.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

The present invention is described herein, in an exemplary manner, with reference to computer system architecture and exemplary processes carried out by the computer system. In one or more embodiments, the functionality described herein can be implemented by computer system instructions. These computer program instructions may be loaded directly onto an internal data storage device of a computing device (e.g., an internal data storage device of a laptop computing device and/or a data processing device within a head-mounted display). Alternatively, these computer program instructions could be stored on a portable computer-readable medium (e.g., a flash drive, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software.

This description describes in general form the computer program(s) required to carry out the functionality of the head-mounted display system described herein. Any competent programmer in the field of information technology could develop a system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. In addition to that which is explicitly depicted, it is to be understood that many alternative or additional functional relationships and/or physical connections may be incorporated in a practical application of the system.

1. Illustrative Head-Mounted Display System

Figure 1:
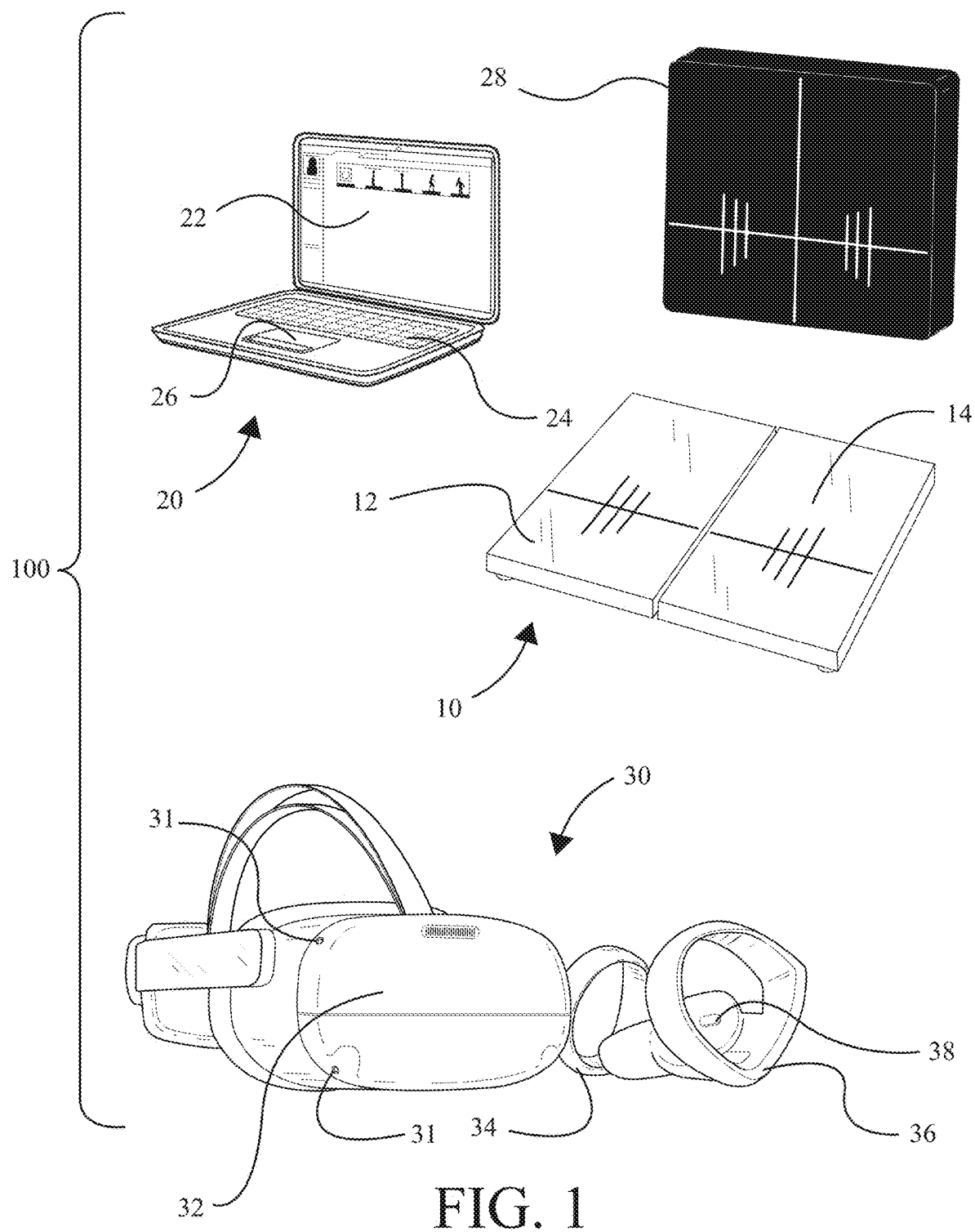
FIG. 1 is a perspective view of a head-mounted display system, according to an illustrative embodiment of the invention.
Figure 2:
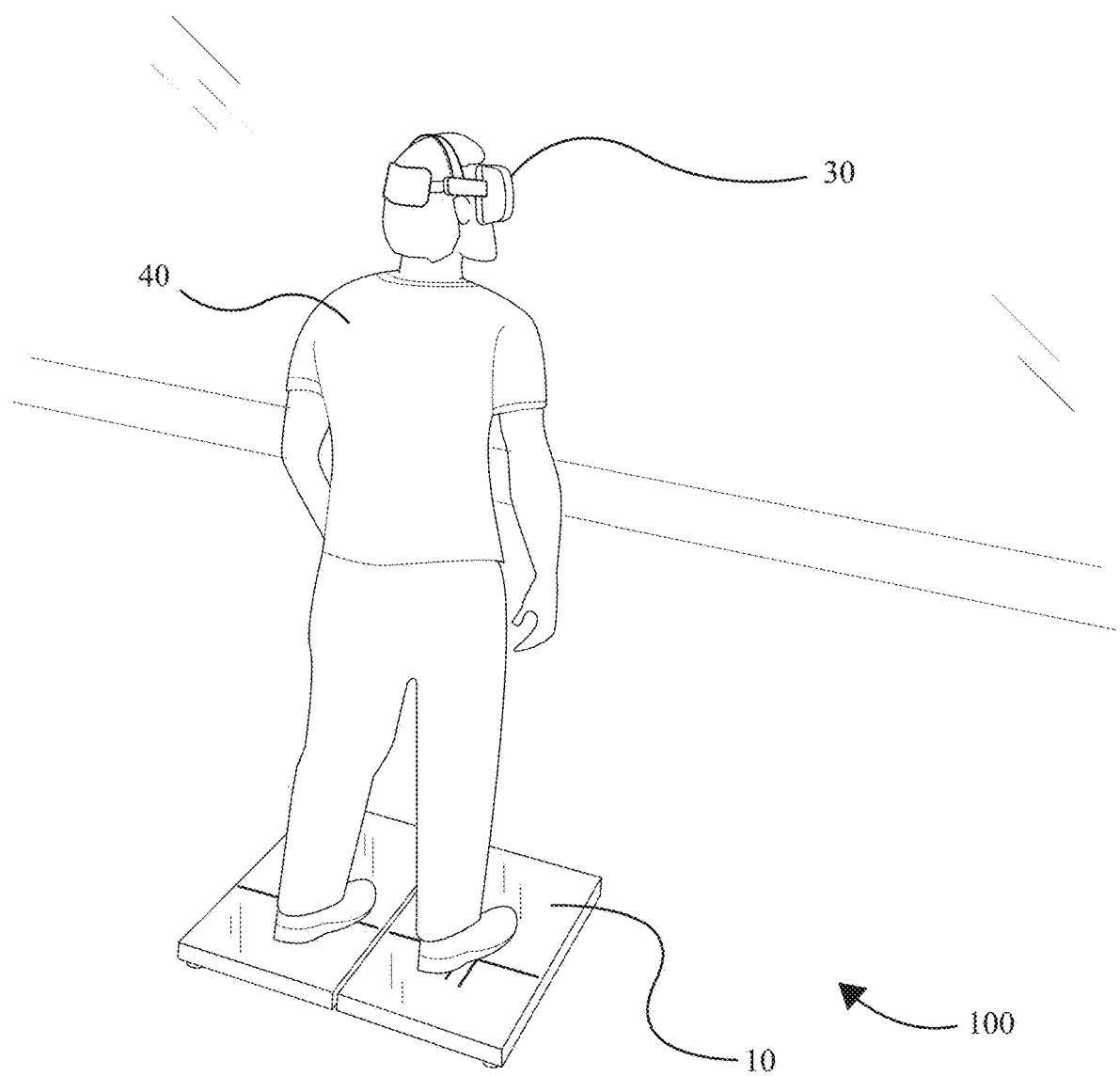
FIG. 2 is a perspective view of a user disposed on a force measurement device and wearing the head-mounted visual display device of the head-mounted display system, according to an illustrative embodiment of the invention.

An illustrative embodiment of a head-mounted display (HMD) system is seen generally at 100 in FIGS. 1 and 2. In the illustrative embodiment, the head-mounted display system 100 comprises a head-mounted display 30 configured to be worn on a head of a user (e.g., a patent or subject). In the illustrative embodiment of FIG. 1, the head-mounted display 30 has a visual display device 32 located in the front of the headset 30. In the illustrative embodiment, the screen images of the training modes described hereinafter are displayed on visual display device 32 of the head-mounted display 30 so that the user is able to interact with one or more visual objects in the screen images. Also, in the illustrative embodiment, the head-mounted display 30 may comprise tracking cameras, one or more microphones, a Universal Serial Bus Type C (USB-C) interface, one or more status indicator lights, and a plurality of user buttons (e.g., a power button, an app/back button, a home button, and a confirm button). The head-mounted display 30 may include an integral data processing device that is capable of carrying out all of the functionality described herein (e.g., the training routines and tests described hereinafter).

In the illustrative embodiment, the head-mounted display 30 may have the following exemplary specifications: (i) a single liquid crystal display (LCD) binocular display, (ii) a resolution of at least 1830×1920 per eye, (iii) a refresh rate of at least 90 Hz, (iv) a horizontal visible field of view (FOV) of at least 98 degrees, (v) a vertical visible field of view (FOV) of at least 90 degrees, (vi) a built-in eye tracking device, (vii) a Qualcomm Snapdragon 865 chip set, (viii) at least 6 GB memory, and (ix) at least 128 GB storage.

Referring again to the illustrative embodiment of FIG. 1, it can be seen that the head-mounted display system 100 may further include a laptop computing device 20 (i.e., a data processing device or computing device that is separate from the head-mounted display 30). Similar to the data processing device in the head-mounted display 30, the laptop computing device 20 also may be capable of carrying out all of the functionality described herein (e.g., the training routines and tests described hereinafter).

In addition, as shown in the illustrative embodiment of FIG. 1, the head-mounted display system 100 further includes one or more user input devices 34, 36. The user input devices 34, 36 are configured to output signals based upon input responses by a user. For example, when the user displaces and/or rotates the user input devices 34, 36, output signals are generated based on the movements of the user. In the illustrative embodiment, the user input devices 34, 36 may be in a form of right and left hand controllers that are worn on the respective hands of the user to interact with the screen images displayed on the visual display device 32 of the head-mounted display 30. Each hand controller 34, 36 also may include one or more buttons 38 for enabling the user to interact with the screen images displayed on the visual display device 32. In the illustrative embodiment, the head position sensing device (e.g., an inertial measurement unit) in the head-mounted display 30 may operate as a further input device for enabling the user to interact with the screen images displayed on the visual display device 32 of the head-mounted display 30. In other embodiments, the system 100 may include one or more of the following additional user input devices: (i) a voice recognition device, (ii) a wireless remote control with one or more buttons, (iii) a keyboard (i.e., a virtual or physical keyboard), (iv) a clicking device, (v) a joystick, and (vi) a laser pointing device.

In the illustrative embodiment, while performing the training routines and tests described hereinafter, the user may use the user input devices 34, 36 in order to enter and transmit his or her responses to the at least one data processing device (e.g., to the data processing device in the head-mounted display 30 and/or the remote laptop 20). For example, the user may use the user input devices 34, 36 to select a particular visual object on the output screen of the visual display device 32 of the head-mounted display 30.

In the illustrative embodiment, the head-mounted display system 100 may further include headset auto-discovery and connection functionality. In particular, the software running on the headset 30 may respond to a status ping over standard WiFi networking UDP broadcasts, initiating a connection back to the base station (e.g., the laptop computing device 20) that sent the status ping. This in turn creates a handshaking opportunity for the two systems to negotiate a secure crypto client-server protocol.

In the illustrative embodiment, the head-mounted display system 100 may further include a headset hands-off configuration. In particular, if during the auto discovery and connection, the base station (e.g., the laptop computing device 20) determines that the headset 30 is running outdated software or an updated configuration is needed, the user is prompted to plug the headset 30 into the base station via a standard USB cable. The laptop software will then configure the headset 30 and restart it, performing all needed updates and configuration steps without the user's involvement or actions (typically, this would need the user to wear the headset and use the controllers to navigate through several sub-menus and programs, and copy files from the computer or USB thumb drive into the headset). In the illustrative embodiment, the total automated configuration time is normally under two (2) minutes.

Figure 3:
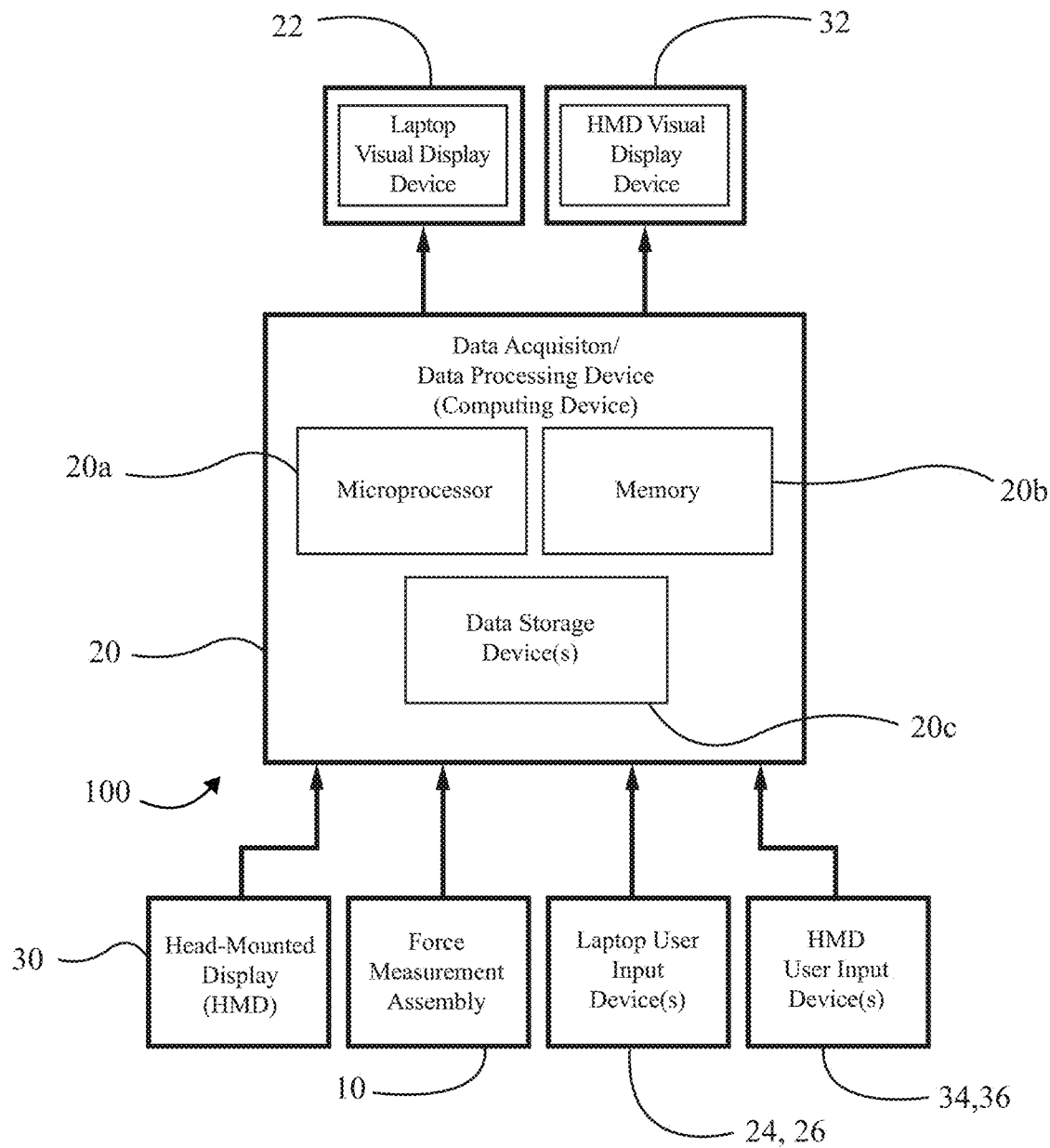
FIG. 3 is a block diagram of constituent components that may be utilized in the illustrative embodiment of the head-mounted display system described herein.

Now, turning again to the illustrative embodiment of FIG. 3, it can be seen that the at least one data processing device (e.g., the laptop computing device 20) of the head-mounted display system 100 comprises a microprocessor 20a for processing data, memory 20b (e.g., random access memory or RAM) for storing data during the processing thereof, and data storage device(s) 20c, such as one or more internal solid state drives, external flash drives, or any combination thereof. As shown in FIG. 3, the laptop visual display device 22 and the HMD visual display device 32 are operatively coupled to the computing device 20 such that data is capable of being transferred between these devices. In the illustrative embodiment, the laptop visual display device 22 may be a touchscreen visual display device with a touchscreen user interface. Also, as illustrated in FIG. 3, one or more laptop user input devices 24, 26, such as the integral keyboard 24 and touchpad 26, are operatively coupled to the computing device 20 so that a user is able to enter data into the computing device 20. In one or more alternative embodiments, the computing device 20 may be in the form of a tablet computing device, a desktop computer, or a smartphone, rather than the laptop computing of the illustrative embodiment.

Referring again to FIGS. 1-3, it can be seen that the illustrative head-mounted display system 100 may further include a force measurement assembly 10 for measuring the ground reaction forces and/or moments of the user. In particular, the force measurement assembly 10 may comprise a static dual force plate or balance plate that is configured to rest on the floor of the room in which the system 100 is disposed. The dual force plate 10 comprises a plurality of force transducers or load cells for measuring the forces and/or moments generated on the two plate surfaces thereof by respective feet of the user. As such, the center of pressure (COP), center of gravity (COG), and/or sway angle of the user may be determined while the user undergoes training on the force measurement assembly 10. For example, in the illustrative embodiment, the dual force plate 10 may use the force plate technology described in U.S. Pat. No. 8,544,347, the entire disclosure of which is incorporated herein by reference. As shown in FIG. 1, the head-mounted display system 100 may further comprise a foam pad 28 that is placed on top of the force measurement assembly 10 for creating instability during the balance testing of the user 40 (i.e., the user 40 stands on the foam pad 28 disposed on the top of the force measurement assembly 10 during such a balance test).

In the illustrative embodiment, the force measurement assembly 10 is operatively coupled to the data processing device 20 by virtue of an electrical cable. In one embodiment, the electrical cable is used for data transmission, as well as for providing power to the force measurement assembly 10. Various types of data transmission cables can be used for the cable of the force measurement assembly 10. For example, the cable can be a Universal Serial Bus (USB) cable or an Ethernet cable. Preferably, the electrical cable contains a plurality of electrical wires bundled together, with at least one wire being used for power and at least another wire being used for transmitting data. The bundling of the power and data transmission wires into a single electrical cable advantageously creates a simpler and more efficient design. In addition, it enhances the safety of the training environment for the user. However, it is to be understood that the force measurement assembly 10 can be operatively coupled to the data processing device 20 using other signal transmission means, such as a wireless data transmission system. If a wireless data transmission system is employed, it is preferable to provide the force measurement assembly 10 with a separate power supply in the form of an internal power supply or a dedicated external power supply.

Now, the acquisition and processing of the load data carried out by the illustrative embodiment of the head-mounted display system 100 will be described. Initially, a load is applied to the force measurement assembly 10 by the user disposed thereon. The load is transmitted from the first and second plate components 12, 14 of the dual force plate 10 to its force transducer beams. In the illustrative embodiment, each plate component 12, 14 of the dual force plate 10 is supported on a pair of force transducer beams disposed thereunder. In the illustrative invention, each of the force transducer beams includes a plurality of strain gages wired in one or more Wheatstone bridge configurations, wherein the electrical resistance of each strain gage is altered when the associated portion of the associated beam-type force transducer undergoes deformation (i.e., a measured quantity) resulting from the load (i.e., forces and/or moments) acting on the first and second plate components 12, 14. For each plurality of strain gages disposed on the force transducer beams, the change in the electrical resistance of the strain gages brings about a consequential change in the output voltage of the Wheatstone bridge (i.e., a quantity representative of the load being applied to the measurement surface). Thus, in the illustrative embodiment, the pair of force transducer beams disposed under the plate components 12, 14 output a total of six (6) analog output voltages (signals). In the illustrative embodiment, the six (6) analog output voltages from dual force plate are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 10 transmits the force plate output signals $S_{FPO1}$-$S_{FPO6}$ to a main signal amplifier/converter. Depending on whether the preamplifier board also includes an analog-to-digital (A/D) converter, the force plate output signals $S_{FPO1}$-$S_{FPO6}$ could be either in the form of analog signals or digital signals. The main signal amplifier/converter further magnifies the force plate output signals $S_{FPO1}$-$S_{FPO6}$, and if the signals $S_{FPO1}$-$S_{FPO6}$ are of the analog-type (for a case where the preamplifier board did not include an analog-to-digital (A/D) converter), it may also convert the analog signals to digital signals. In the illustrative embodiment, the force plate output signals $S_{FPO1}$-$S_{FPO6}$ may also be transformed into output forces and/or moments (e.g., $F_{Lz}$, $M_{Lx}$, $M_{Ly}$, $F_{Rz}$, $M_{Rx}$, $M_{Ry}$) by the firmware of the dual force plate by multiplying the voltage signals $S_{FPO1}$-$S_{FPO6}$ by a calibration matrix prior to the force plate output data being transmitted to the data processing device 20. Alternatively, the data acquisition/data processing device 20 may receive the voltage signals $S_{FPO1}$-$S_{FPO6}$, and then transform the signals into output forces and/or moments (e.g., $F_{Lz}$, $M_{Lx}$, $M_{Ly}$, $F_{Rz}$, $M_{Rx}$, $M_{Ry}$) by multiplying the voltage signals $S_{FPO1}$-$S_{FPO6}$ by a calibration matrix.

After the voltage signals $S_{FPO1}$-$S_{FPO6}$ are transformed into output forces and/or moments (e.g., $F_{Lz}$, $M_{Lx}$, $M_{Ly}$, $F_{Rz}$, $M_{Rx}$, $M_{Ry}$), the center of pressure for each foot of the user (i.e., the x and y coordinates of the point of application of the force applied to the measurement surface by each foot) may be determined by the data acquisition/data processing device 20. If the force transducer technology described in U.S. Pat. No. 8,544,347 is employed, it is to be understood that the center of pressure coordinates ($x_{P_L}$, $y_{P_L}$, $x_{P_r}$, $x_{P_r}$) can be computed in the particular manner described in that patent. Also, as described below, rather than computing two sets of center of pressure coordinates (i.e., one for each foot of the user), a single set of overall center of pressure coordinates ($x_p$, $y_p$) may be computed in one or more embodiments.

In one or more alternative embodiments, the data processing device 20 determines the vertical forces $F_{Lz}$, $F_{Rz}$ exerted on the surface of the first and second force plates by the feet of the user and the center of pressure for each foot of the user, while in another embodiment where a six component force plate is used, the output forces of the data processing device 20 includes all three (3) orthogonal components of the resultant forces acting on the two plate components 12, 14 (i.e., $F_{Lx}$, $F_{Ly}$, $F_{Lz}$, $F_{Rx}$, $F_{Ry}$, $F_{Rz}$) and all three (3) orthogonal components of the moments acting on the two plate components 12, 14 (i.e., $M_{Lx}$, $M_{Ly}$, $M_{Lz}$, $M_{Rx}$, $M_{Ry}$, $M_{Rz}$ In yet other embodiments of the invention, the output forces and moments of the data processing device 20 can be in the form of other forces and moments as well.

In the illustrative embodiment, where a single set of overall center of pressure coordinates ($x_p$, $y_p$) are determined for the force measurement assembly 10, the center of pressure of the force vector $\vec{F}$ applied by the user to the measurement surface of the force plate 22 is computed as follows:

$$x_P = \frac{-M_y}{F_Z} \tag{1}$$

-continued $$y_P = \frac{M_x}{F_Z} \quad (2)$$

where:

$x_p$, $y_p$: coordinates of the point of application for the force (i.e., center of pressure) on the force plate assembly 10;

$F_z$: z-component of the resultant force acting on the force plate assembly 10;

$M_x$: x-component of the resultant moment acting on the force plate assembly 10; and $M_y$: y-component of the resultant moment acting on the force plate assembly 10.

In addition, in a further embodiment, the head-mounted display system 100 further comprises a data interface configured to operatively couple the data processing device 20 to a remote computing device (e.g., remote laptop or desktop computing device) so that data from the data processing device 20 is capable of being transmitted to the remote computing device. In one or more embodiments, the data interface may comprise a wireless data interface or a wired data interface operatively coupling the data processing device 20 to the remote computing device.

2. Testing and Training Functionality of the Head-Mounted Display System

Now, with reference to the screen images of FIGS. 4-17, the testing and training functionality carried out by the head-mounted display system 100 will be described in detail. In the illustrative embodiment, the first data processing device of the head-mounted visual display device 30 and/or the second data processing device (i.e., laptop computing device 20) is programmed to execute each of the training modes described hereinafter.

Figure 4:
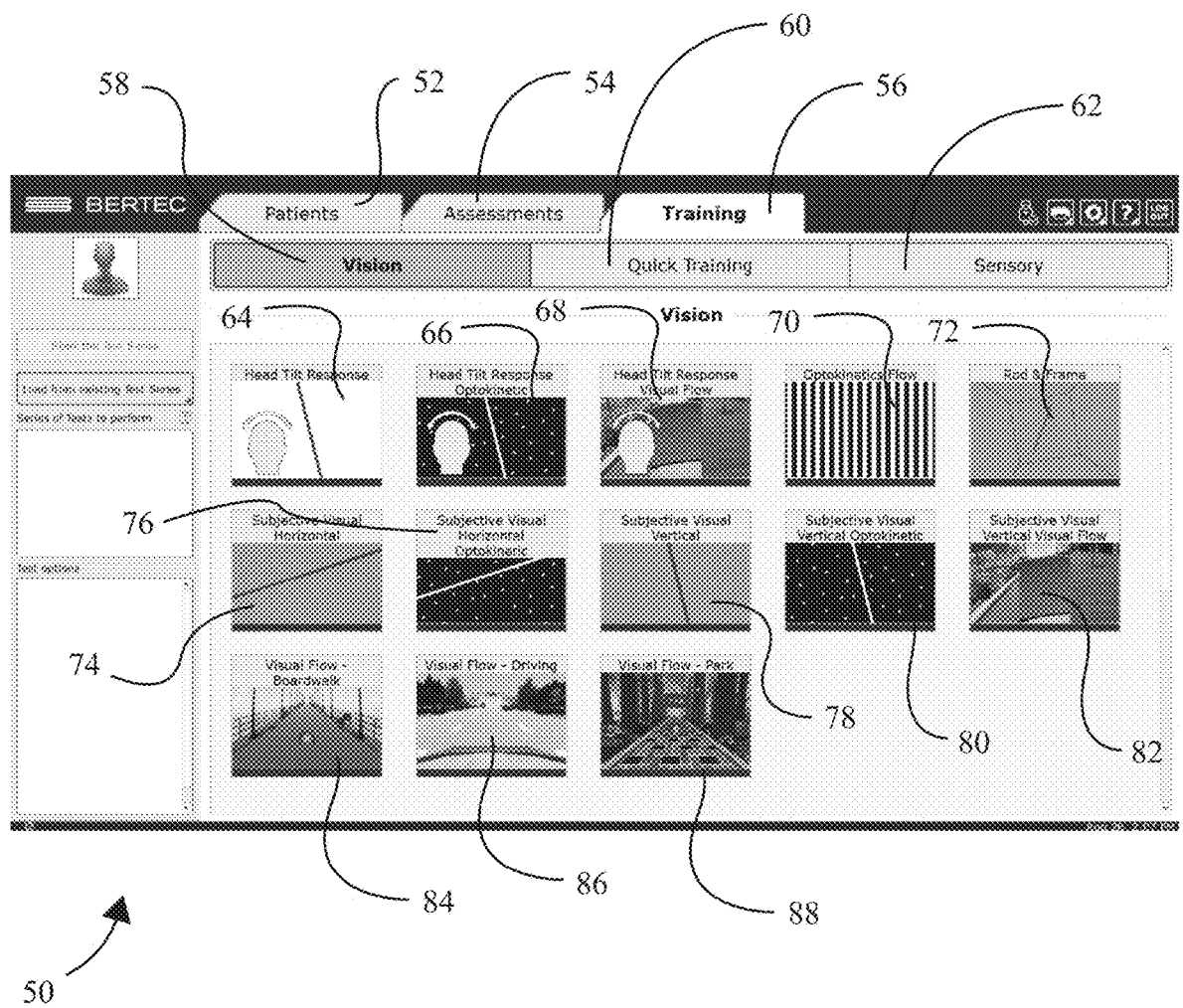
FIG. 4 is a screen image of an operator/clinician home screen of the head-mounted display system, according to an illustrative embodiment of the invention.

An exemplary screen image of an operator/clinician home screen 50 of the head-mounted display system 100 is shown in FIG. 4. As shown in this figure, the operator/clinician home screen 50 includes: (i) a "Patients" tab 52, (ii) an "Assessments" tab 54, and (iii) a "Training" tab 56. In the exemplary screen image of FIG. 4, the "Training" tab 56 has been selected. The "Training" tab 56 of the operator/clinician home screen 50 includes the following sub-tabs: (i) a "Vision" sub-tab 58, (ii) a "Quick Training" sub-tab 60, and (iii) a "Sensory" sub-tab 62. In the exemplary screen image of FIG. 4, the "Vision" sub-tab 58 has been selected. The "Vision" sub-tab 58 of the operator/clinician home screen 50 includes the following icons: (i) a "Head Tilt Response" icon 64, (ii) a "Head Tilt Response Optokinetic" icon 66, (iii) a "Head Tilt Response Visual Flow" icon 68, (iv) a "Optokinetics Flow" icon 70, (v) a "Rod & Frame" icon 72, (vi) a "Subjective Visual Horizontal" icon 74, (vii) a "Subjective Visual Horizontal Optokinetic" icon 76, (viii) a "Subjective Visual Vertical" icon 78, (ix) a "Subjective Visual Vertical Optokinetic" icon 80, (x) a "Subjective Visual Vertical Visual Flow" icon 82, (xi) a "Visual Flow—Boardwalk" icon 84, (xii) a "Visual Flow—Driving" icon 86, and (xiii) a "Visual Flow—Park" icon 88. When a user clicks on one of the icons 64-88 in the vision training selection menu, he or she is directed to the selected training routine.

Figure 5:
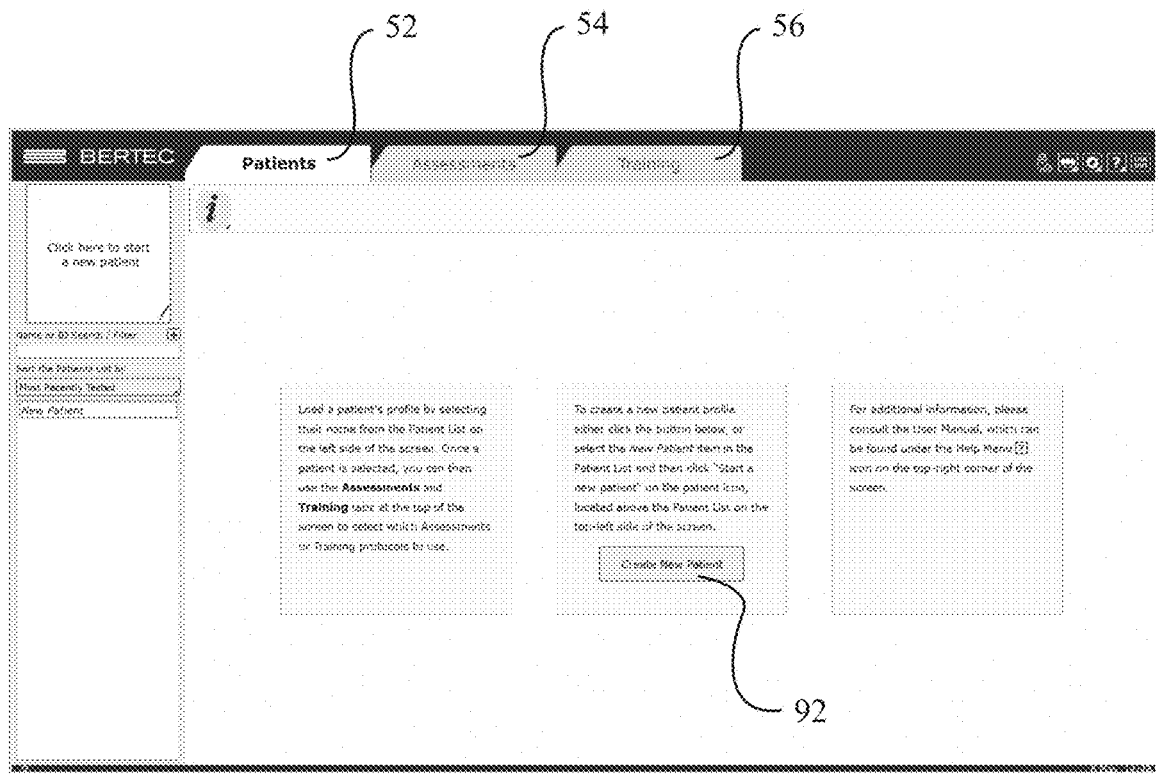
FIG. 5 is a screen image of a patient tab of the head-mounted display system, according to an illustrative embodiment of the invention.

Turning to FIG. 5, the "Patients" tab 52 on the operator/clinician home screen 50 has been selected by a user. As shown in this figure, the "Patients" screen 90 include a plurality of instructions for the user and a "Create New Patient" button 92, which can be selected in order to create a new patient profile.

In the first set of training routines carried out by the illustrative head-mounted display system 100, the user input device comprises one or more hand controllers 34, 36 of the head-mounted visual display device 30, and the input signal to the at least one data processing device (i.e, first data processing device and/or second data processing device) comprises one or more hand control signals outputted by the one or more hand controllers 34, 36. The one or more hand control signals are generated based upon a hand movement of the user. The at least one data processing device is configured to receive the one or more hand control signals that are generated based upon the hand movement of the user, and to control the movement of at least one displaceable visual object on the output screen 32 of the head-mounted visual display device 30 towards at least one visual target.

In particular, in one subset of the first set of illustrative training routines, the visual scene on the visual display device 32 of the head-mounted display 30 is designed to assess the user's ability to align a rod with respect to the gravitational vertical (0°) or horizontal by using the hand controller 34, 36 or middle finger trigger of the controller. The objective is for the user to use the controller 34, 36 to align the rod with respect to the gravitational vertical (SVV and R&F) or horizontal (SVH) in a fully immersive virtual reality (VR) scene. In these training routines, the at least one data processing device is configured to determine how closely the user is able to align the at least one displaceable visual object (e.g., the rod) relative to the at least one visual target (gravitational vertical or horizontal). During the training routines, the user (e.g., the patient) is asked to use the right and/or left controllers 34, 36 to position the rod at the gravitational vertical or horizontal. He or she will submit their response by using the index trigger button 38. Once the response is submitted, the correct rod angle will display. Both rods will then disappear, and a new rod will show. Various levels of difficulty can be implemented with optokinetic and visual flow options.

In the illustrative embodiment, the operator can choose from different optokinetic scenes that will be used in the background of the rod (e.g., stripped or starfield). Also, the operator can define the color of the rod (e.g., black, red, or green). The operator additionally can define the direction of the optokinetic movement (e.g., up, down, left, right), the speed of the optokinetic movement (e.g., speed ranges from 0-25 in increments of 5), the density of the optokinetic scene (e.g., low, medium, or high).

In the illustrative embodiment, the operator can choose the type of visual flow scene that will be used in the background of the rod (e.g., park, boardwalk, or driving). Also, the operator can define the speed of the scene's movement (e.g., slow, medium, or fast).

In another one of the first set of illustrative training routines, the user is positioned either sitting or standing, with the headset 30 on and the controllers 34, 36 in the correct hands. The user is shown a sequence of items 144, 146 sitting on a grocery store shelf 142 (see screen image 140 in FIG. 13). These items 144, 146 are introduced in a particular order and will appear for a couple of seconds and disappear. Then, the user identifies the items on the shelf 142 using the handheld controllers 34, 36 in the same sequence they were initially presented by selecting each item 148. In this training routine, the at least one visual target generated and displayed on the output screen by the at least one data processing device comprises a plurality of visual targets 144, 146 displayed in a particular sequence on the output screen. The at least one data processing device is configured to determine whether the user is able to correctly identify the plurality of visual targets 144, 146 displayed in the particular sequence when the user selects the plurality of visual targets using the at least one displaceable visual object 148 on the output screen. If the user gets the sequence correct, he or she moves to the next level. If he or she gets the sequence incorrect, he or she will move back one level. In the illustrative embodiment, the user will continue until he or she gets a total of three incorrect sequences. The objective is to get to the highest level possible, by identifying multiple sequences in the same order as they were initially presented.

In yet another one of the first set of illustrative training routines, the user is positioned either sitting or standing, with the headset 30 on and the controllers 34, 36 in the correct hands. The user is shown several items 154, 156 on a grocery shelf 152 at the same time (see screen image 150 in FIG. 14). The items 154, 156 will appear for a couple of seconds and disappear. After the items have disappeared, items will be present on the shelf again, and the user will be required to identify the same items that were originally on the shelf. In this training routine, the at least one visual target generated and displayed on the output screen by the at least one data processing device comprises a plurality of visual targets 154, 156 displayed in a predetermined pattern on the output screen for a predetermined period of time. The at least one data processing device is configured to determine whether the user is able to correctly identify the plurality of visual targets 154, 156 displayed in the predetermined pattern when the user selects the plurality of visual targets using the at least one displaceable visual object on the output screen. If the user gets the sequence correct, he or she will move to the next level, if he or she gets the sequence incorrect, he or she will move back one level. In the illustrative embodiment, the user will continue until they get a total of three incorrect sequences. The objective is to get to the highest level possible by identifying items on the shelf 152 that were previously highlighted.

In still another one of the first set of illustrative training routines, the user is either sitting or standing with the headset 30 on and the controllers 34, 36 in the correct hands. He or she is shown a grocery store shelf 162 with an item 164 on it that will be randomly highlighted in one of two colors (see screen image 160 in FIG. 15). If the object 164 is highlighted in green, the user is to touch 166 the item as quickly as possible. If the item 164 is highlighted red, the user should not select the item. After one object 164 is highlighted, the highlight will disappear from that object 164 and a new object will become highlighted. In this training routine, the at least one visual target 164 generated and displayed on the output screen by the at least one data processing device comprises a first visual object having a first color (e.g., green) or shape and then a subsequently displayed second visual object having a second color (e.g., red) or shape. The first color or shape is different from the second color or shape. When the user is presented with the first visual object having the first color or shape, the at least one data processing device is programmed to determine whether the user performs a correct action by selecting the first visual object. When the user is presented with the second visual object having the second color or shape, the data processing device is programmed to determine whether the user performs a correct action by not selecting the second visual object. The objective in this training routine is to hit the "go" (green highlighted) object as quickly as possible and to avoid hitting the "No-go" (red highlighted) object.

In yet another one of the first set of illustrative training routines, the user is either sitting or standing with the headset 30 on and the controllers 34, 36 in the correct hands. A grocery store shelf scene will be displayed on the headset 30 (see screen image 170 in FIG. 16). One of the objects 174 on the shelf 172 will randomly be highlighted and the objective of the user is to touch the highlighted item 174 as quickly as he or she can (e.g., with virtual hand selector 176 in FIG. 16). When an item 174 is "hit" a new item will appear, and the user is to hit as many items as they can in the given time. In this training routine, the at least one visual target generated and displayed on the output screen by the at least one data processing device comprises a plurality of visual targets displayed on the output screen, and the at least one data processing device is further configured to randomly mark one 174 of the plurality of visual targets and determine how quickly the user is able to correctly identify the marked one 174 of the plurality of visual targets on the output screen.

Figure 17:
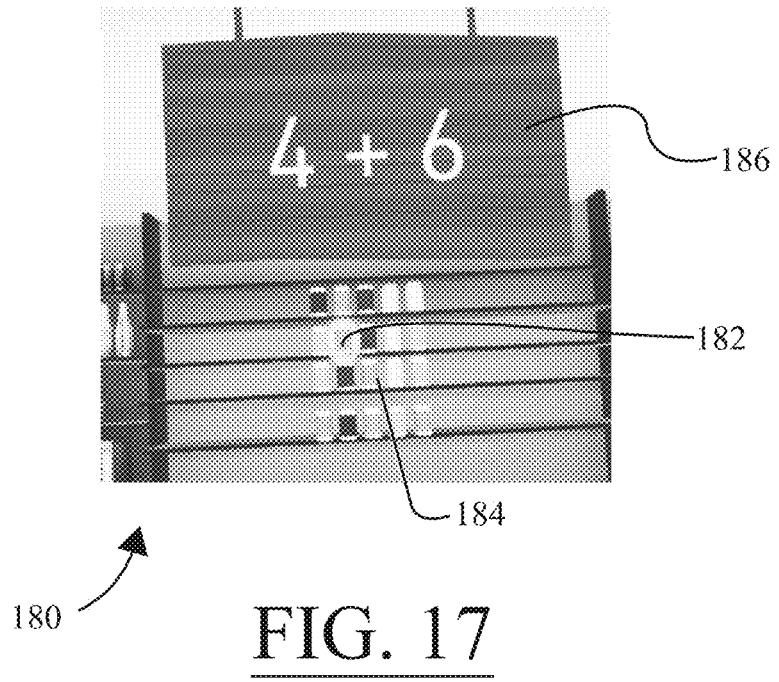
FIG. 17 is a screen image of a fifth sensory training routine of the head-mounted display system, according to an illustrative embodiment of the invention.

With reference to the screen image 180 in FIG. 17, in a further illustrative embodiment of this training routine, there is a dual task feature that includes a cognitive task 186 above the shelf 184 of the grocery items 182. For example, the cognitive task options may include: (i) stroop congruent, (ii) stroop incongruent, (iii) stroop random, and (iv) math. The operator will record correct/incorrect tasks with their remote control. This dual task feature also may be available with a laser input method. For this dual task feature, the at least one data processing device is further configured to generate and display a cognitive task 186 on the output screen of the head-mounted display system 100 together with the plurality of visual targets, and to determine whether the user is able to correctly perform the cognitive task when identifying the marked one 182 of the plurality of visual targets on the output screen.

In the second set of training routines carried out by the illustrative head-mounted display system 100, the user input device comprises a force measurement assembly 10 (see e.g., user 40 disposed on dual force plate 10) and the input signal comprises one or more measurement signals outputted by one or more force measurement devices of the force measurement assembly. The one or more measurement signals are generated based upon the user's contact with a surface of the force measurement assembly 10. The at least one data processing device is configured to receive the one or more measurement signals that are generated based upon the user's contact with the surface of the force measurement assembly 10 and to compute one or more numerical values using the one or more measurement signals. The data processing device is configured to control the movement of the at least one displaceable visual object on the output screen 32 of the head-mounted visual display device 30 towards the at least one visual target by using the one or more computed numerical values.

In the second set of training routines carried out by the illustrative head-mounted display system 100, the center of pressure (center-of-gravity) of the user, which is determined by the at least one data processing device from the force and moment output data of the force measurement assembly 10 described above, is used to control the displacement of a visual object (e.g., a cursor) on the output screen 32 of the head-mounted visual display device 30.

Figure 6:
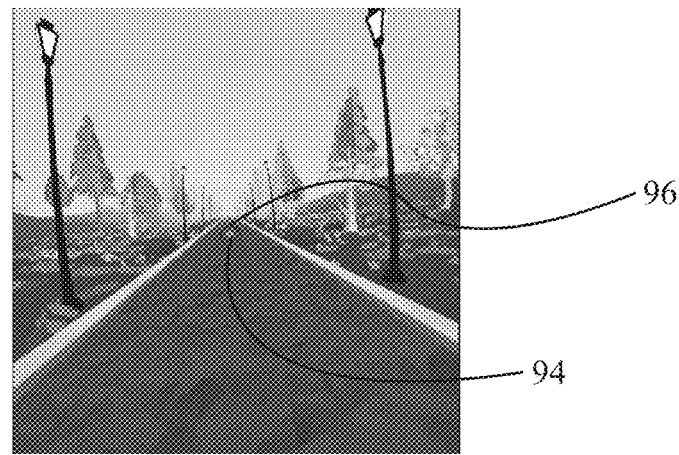
FIG. 6 is a screen image of a first visual flow training routine of the head-mounted display system, according to an illustrative embodiment of the invention.
Figure 7:
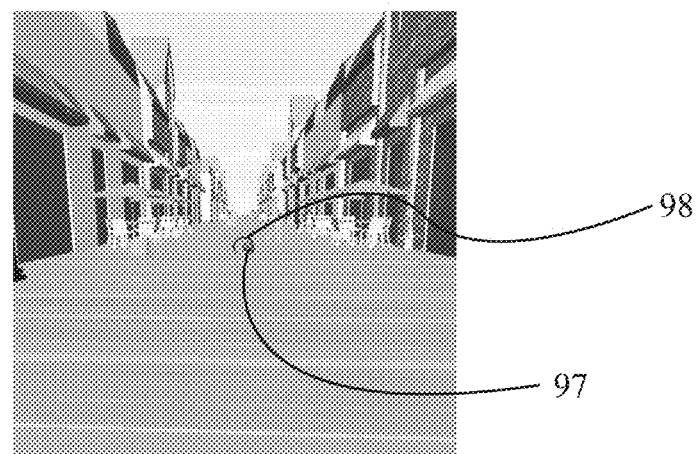
FIG. 7 is a screen image of a second visual flow training routine of the head-mounted display system, according to an illustrative embodiment of the invention.
Figure 8:
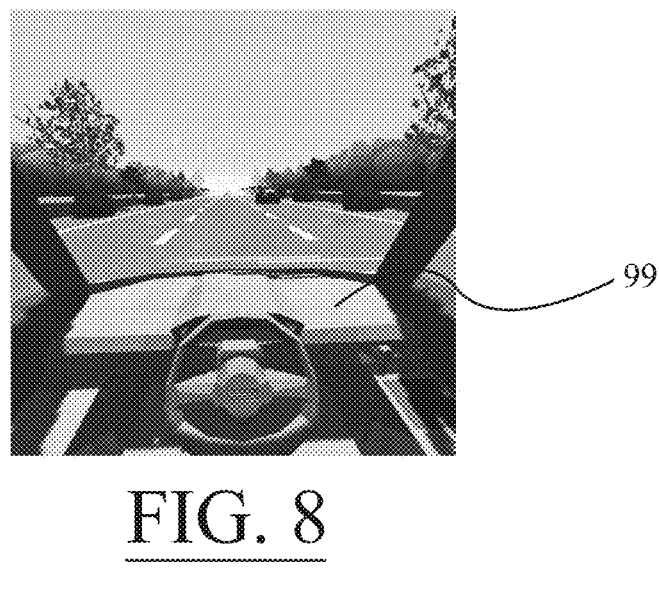
FIG. 8 is a screen image of a third visual flow training routine of the head-mounted display system, according to an illustrative embodiment of the invention.

In particular, in one subset of the second set of illustrative training routines, the user is asked to maintain balance throughout a moving scene while having the option of dodging objects by shifting his or her center-of-gravity (COG), answering simple questions, various distractions, and noise distractions. In this training routine, the at least one data processing device is configured to generate and display a displaceable scene (see e.g., FIGS. 6-8) on the output screen 32 of the head-mounted visual display device 30, and the at least one visual target 96, 98 is superimposed on the displaceable scene. The objective in this training routine is for the user to utilize his or her center-of-gravity (COG) to maintain balance and shift around the box targets if/when they approach using the force measurement assembly 10. The visual scenes are designed to help the user adapt to visual stimuli during balance exercises. In the illustrative embodiment, the operator can choose the type of visual scene that will be used (e.g., park, boardwalk, or driving). In FIG. 6, the park scene 88' is depicted with the circular visual target 96 and the displaceable ball 94 representing the center-of-gravity of the user. In the illustrative park scene, the user is instructed to maintain the displaceable ball 94 within the circular visual target 96 by shifting his or her center-of-gravity in a lateral direction on the force plate 10. In FIG. 7, the boardwalk scene 84' is depicted with the circular visual target 98 and the displaceable ball 97 representing the center-of-gravity of the user. In the illustrative boardwalk scene, the user is instructed to maintain the displaceable ball 97 within the circular visual target 98 by shifting his or her center-of-gravity in a lateral direction on the force plate 10. In FIG. 8, the driving scene 86' is depicted with a car 99 that is controlled by a user shifting his or her center-of-gravity on the force plate 10.

Figure 11:
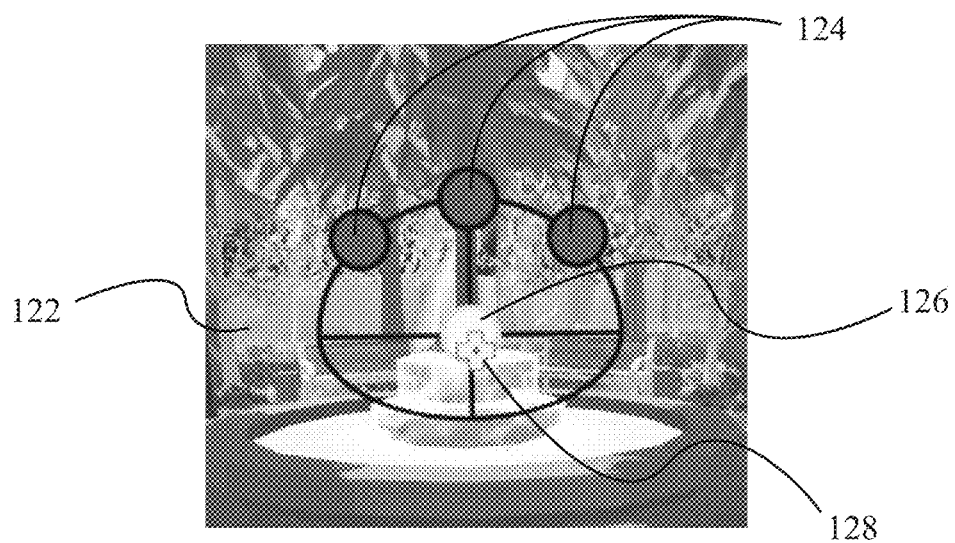
FIG. 11 is a screen image of a first balance quick training routine of the head-mounted display system, according to an illustrative embodiment of the invention.
Figure 12:
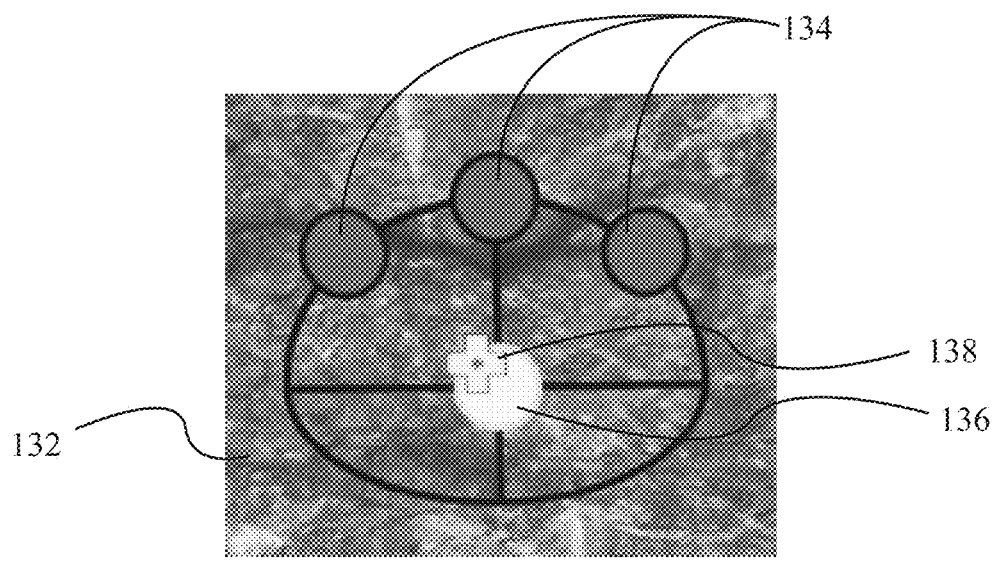
FIG. 12 is a screen image of a second balance quick training routine of the head-mounted display system, according to an illustrative embodiment of the invention.
Figure 13:
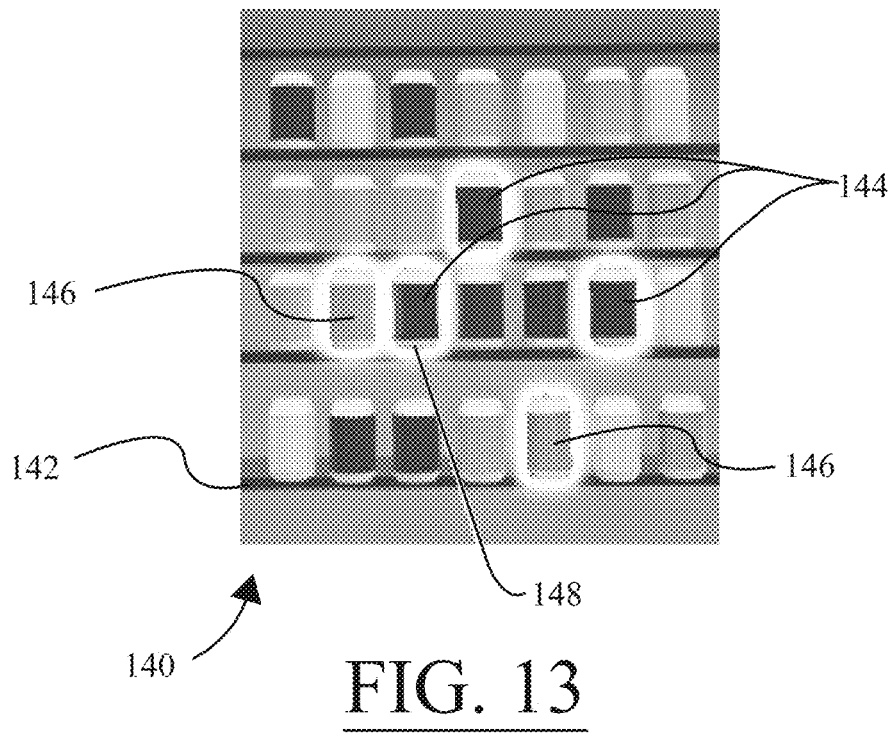
FIG. 13 is a screen image of a first sensory training routine of the head-mounted display system, according to an illustrative embodiment of the invention.
Figure 14:
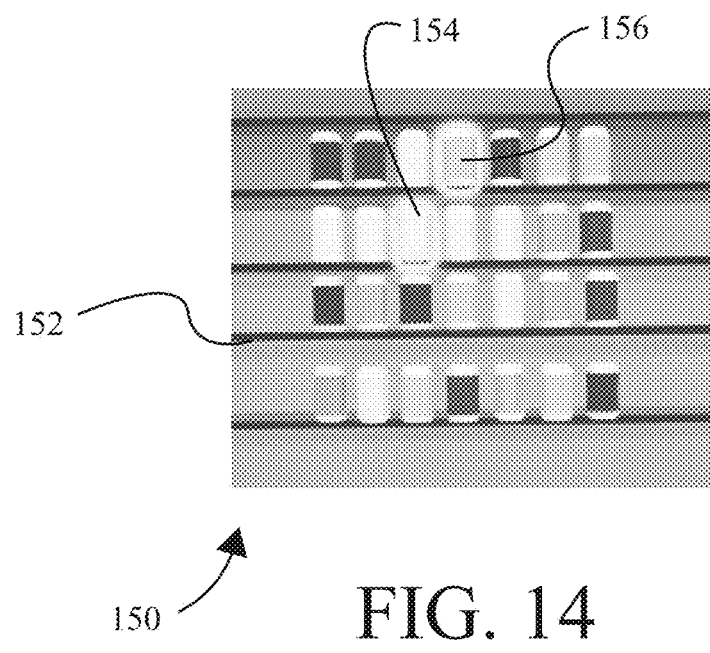
FIG. 14 is a screen image of a second sensory training routine of the head-mounted display system, according to an illustrative embodiment of the invention.
Figure 15:
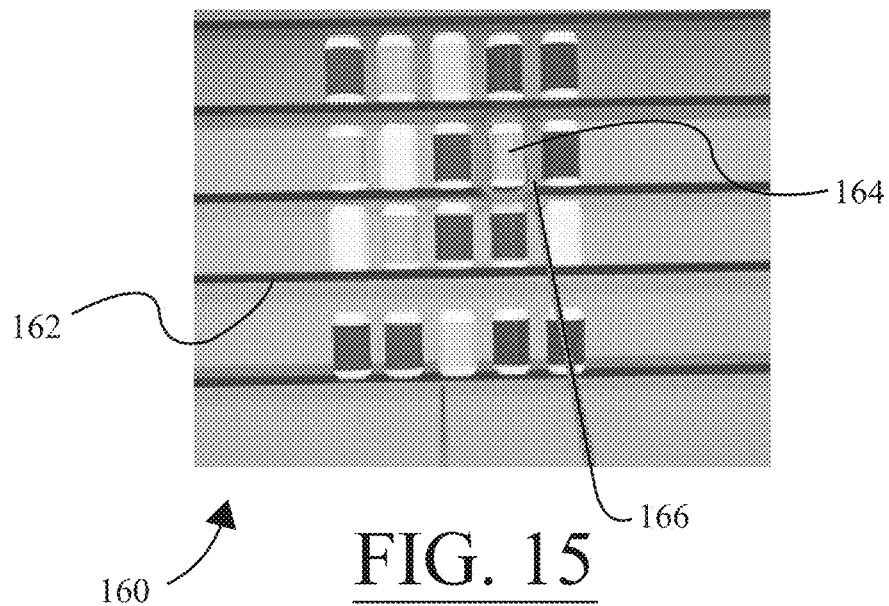
FIG. 15 is a screen image of a third sensory training routine of the head-mounted display system, according to an illustrative embodiment of the invention.
Figure 16:
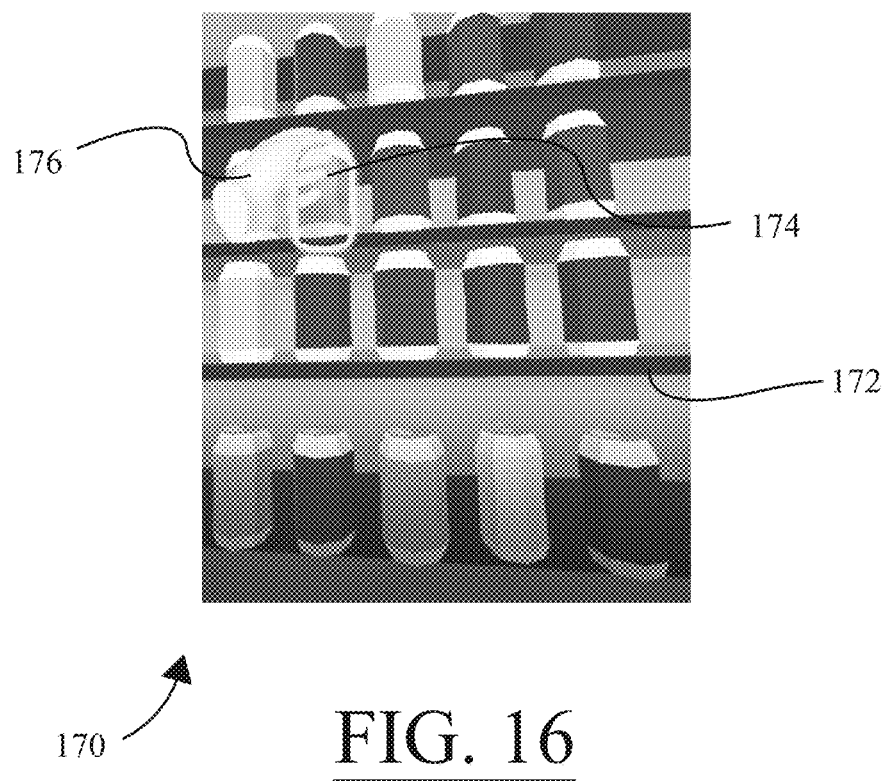
FIG. 16 is a screen image of a fourth sensory training routine of the head-mounted display system, according to an illustrative embodiment of the invention.

In another subset of the second set of illustrative training routines, the user is positioned on the force/balance plate 10 in the correct position and the headset 30 is placed on the user's head. The operator/clinician then chooses one of the quick training protocols and chooses one of the seven scene options. Each protocol has a different target area, and the user is to stay on the balance plate 10 and shift his or her weight towards the plurality of targets being displayed on the headset 30 (see e.g., FIGS. 10-12). In this training routine, the at least one visual target comprises a plurality of visual targets 124, 134 on the output screen 32 of the head-mounted visual display device 30 (see FIGS. 11 and 12). The at least one data processing device is configured to determine how closely the user is able to displace the at least one displaceable visual object (e.g., displaceable cursor 128, 138) to each of the plurality of visual targets 124, 134 on the output screen 32 in succession (see FIGS. 11 and 12). The objective in this training routine is for the user to have easy access to basic training exercises that test balances under distracting stimuli (e.g., virtual reality scenes). The training exercises designed to meet the basic needs of training quickly and easily. In the illustrative embodiment, the operator/clinician can choose the type of virtual reality scene that will be used (e.g., blank field, rock wall, checkered room, moving lines, infinite tunnel, fountain, and airport lounge). In FIG. 11, the fountain scene 120 is depicted with a forest background 122, a fountain with squirting water in the foreground, a plurality of visual targets 124 superimposed on the scene, a displaceable cursor 128 representing the center-of-gravity of the user, and a center location 126 for the cursor 128. In the illustrative fountain scene, the user is instructed to displace the cursor 128 from the center location 126 to each of the visual targets 124 in succession by shifting his or her center-of-pressure on the force plate 10. In FIG. 12, the rock wall scene 130 is depicted with a rock wall background 132, a plurality of visual targets 134 superimposed on the rock wall 132, a displaceable cursor 138 representing the center-of-gravity of the user, and a center location 136 for the cursor 138. In the illustrative rock wall scene, the user is instructed to displace the cursor 138 from the center location 136 to each of the visual targets 134 in succession by shifting his or her center-of-pressure on the force plate 10.

Figure 10:
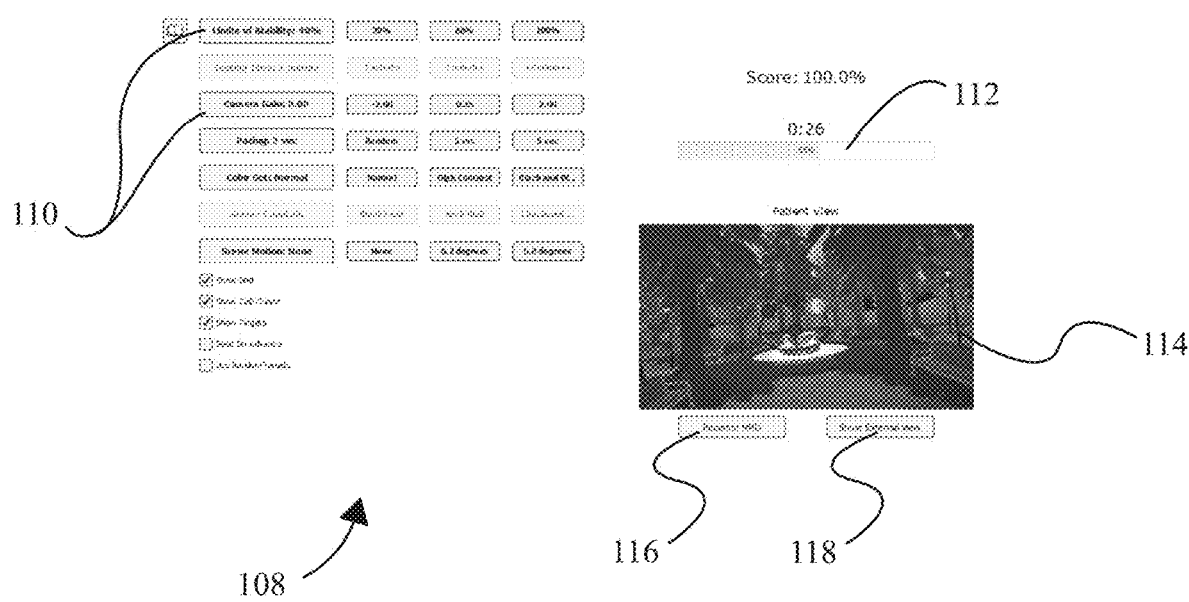
FIG. 10 is a screen image of a quick training clinician screen of the head-mounted display system, according to an illustrative embodiment of the invention.

An exemplary operator/clinician screen 108 for the fountain quick training scene is depicted in FIG. 10. As shown in FIG. 10, the operator/clinician screen 108 comprises setting buttons 110 on the left portion of the screen, a user percentage completion bar 112 in the upper right portion of the screen, and a user screen view 114 in the lower right portion of the screen so that the operator/clinician is able to see what the user is seeing on the output screen 32 of the head-mounted visual display device 30. In FIG. 10, two buttons 116, 118 are provided beneath the user view window 114, namely a "Recenter HMD" button 116 and a "Show External View" button 118.

In the third set of training routines carried out by the illustrative head-mounted display system 100, the user input device comprises a head position sensing device (e.g., an inertial measurement unit for measuring a user's head position, rotation, velocity, and acceleration), and the input signal comprises one or more measurement signals outputted by the head position sensing device. The one or more measurement signals are generated based upon a head movement of the user, and the at least one data processing device is configured to determine a head angle of the user based upon the one or more measurement signals outputted by the head position sensing device. In the illustrative embodiment, the head-mounted visual display device 30 may comprise the head position sensing device (i.e., the head-mounted visual display device 30 may comprise the inertial measurement unit disposed therein).

Figure 9:
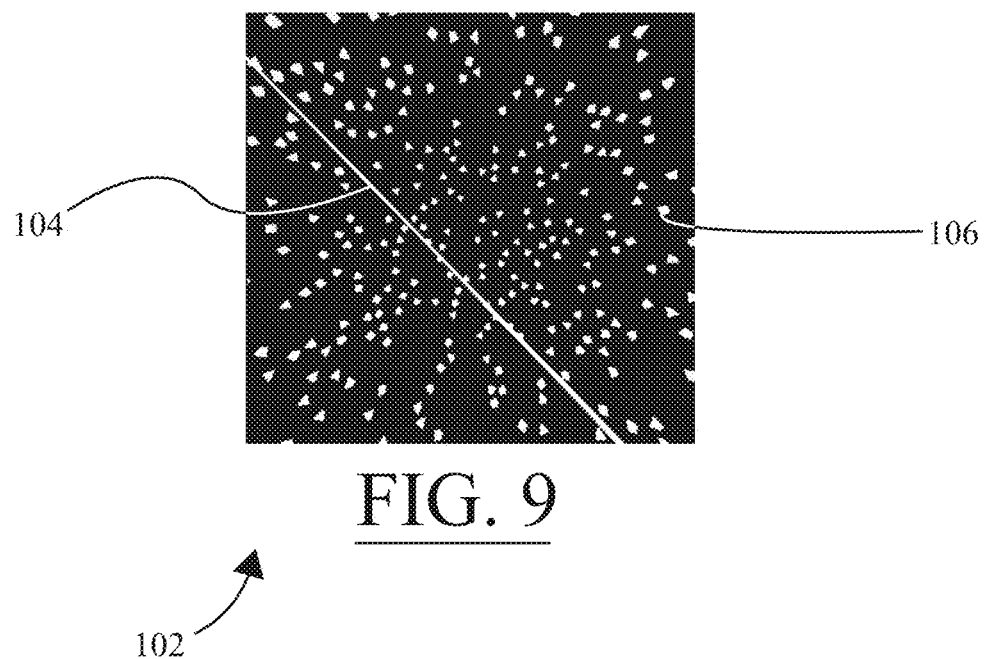
FIG. 9 is a screen image of an optokinetic head tilt response training routine of the head-mounted display system, according to an illustrative embodiment of the invention.

In particular, in one subset of the third set of illustrative training routines, using a rod on the screen, a user must align his or her head with the rod and use the index trigger on the hand controller 34, 36 to submit his or her response when he or she is aligned. In the illustrative embodiment, the rod will disappear on submission and a new rod will appear at a new angle, at which point the user will align with the new rod. This routine continues for the number of trials selected. The objective in this training routine is for the user to tilt his or her head (+/−45 degrees max) to align with the rod or scene inside the headset 30. The visual scene is designed for the user to align his or her head with the rod tilt angle or scene that appears on the screen 32 of the headset 30 while the user is sitting or standing. In the illustrative embodiment, there are three (3) separate Head Tilt Response (HTR) training protocols: (i) head tilt response (HTR), (ii) head tilt response visual flow (HTR-VF), and (iii) head tilt response optokinetics (HTR-OPK). An example of head tilt response optokinetics is shown in FIG. 9. In the head tilt response optokinetics scene 102 of FIG. 9, a rod 104 is superimposed on a star field background 106.

Figure 18:
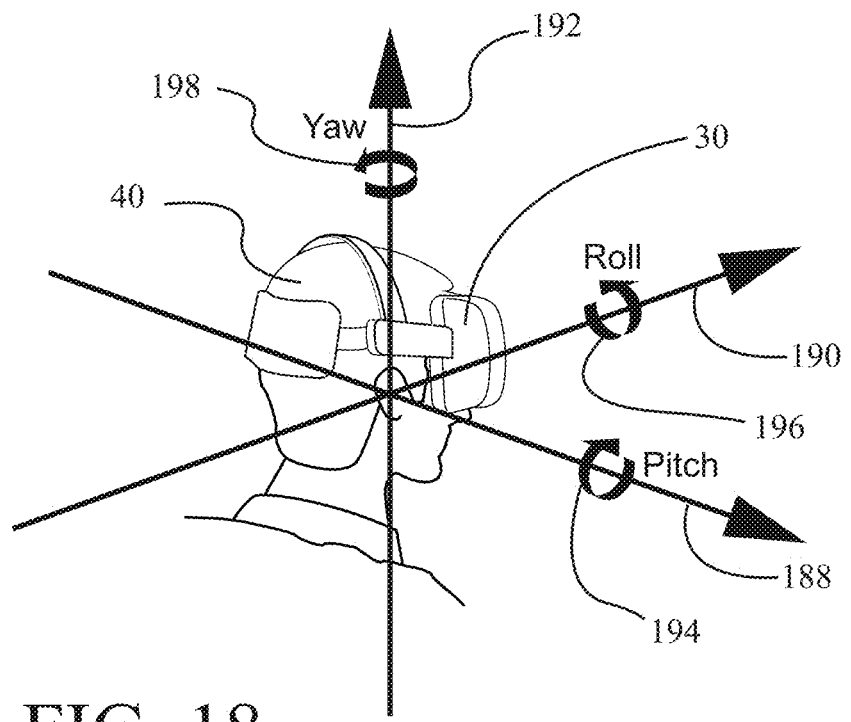
FIG. 18 is a diagrammatic view of the directions of user head rotation that are capable of being measured with the head position sensing device, according to an illustrative embodiment of the invention.

Next, referring to FIG. 18, an explanation of the three (3) directions of head rotation that the head position sensing device of the head-mounted visual display device 30 is capable of detecting will be described. First, the head position sensing device is configured to detect the rotation of the head of the user 40 about the yaw axis 192 of rotation as indicated by the curved arrow 198 in FIG. 18. The curved arrow 198 about the yaw axis 192 indicates the common side-to-side movement of the user's head during the aforedescribed training routines. Secondly, the head position sensing device is configured to detect the rotation of the head of the user 40 about the pitch axis 188 of rotation as indicated by the curved arrow 194 in FIG. 18. The curved arrow 194 about the pitch axis 188 indicates the up-and-down movement of the user's head during the aforedescribed training routines. Thirdly, the head position sensing device is configured to detect the rotation of the head of the user 40 about the roll axis 190 of rotation as indicated by the curved arrow 196 in FIG. 18. The curved arrow 196 about the roll axis 190 indicates the tilt-right and tilt-left movement of the user's head during the aforedescribed training routines.

In a further illustrative embodiment, the head-mounted display system 100 may include headset data collection and synthesis functionality. In particular, during the specific training/test protocols, the headset 30 records and transmits position and rotation values, along with velocity (e.g., now at 5 degrees left and moving at 2.3 degrees per second). The headset 30 also reports eye tracking movement and gaze lingering, along with hand controller position/rotation/velocity. This data from the headset 30 is sampled at a high rate and combined with the force plate data to present a complete 'picture' of the user at any given moment in time (the data rate is sampled at 1000 Hz to match the force plate 10). Combining the data together into existing protocols—e.g., Quick Training where the user must follow the dots by shifting body weight—it can be determined if the user is swaying his or her upper body, turning his or her head to look at the target pattern, and/or if his or her eyes are tracing the displaceable cursor 128, 138 as it moves into the target (or if he or she looks at the target first then move). The visual flow scenes, such as the boardwalk and forest scenes, provide additional opportunities for data synthesis with the eye tracking the various distractors, such as the birds flying through the forest in the forest scene In the third set of illustrative training routines, the inertial measurement unit (IMU) forming the head position sensing device in the headset 30 may comprise a triaxial (three-axis) accelerometer sensing linear acceleration $\vec{\alpha}'$, a triaxial (three-axis) rate gyroscope sensing angular velocity $\vec{\omega}'$, a triaxial (three-axis) magnetometer sensing the magnetic north vector $\vec{n}'$, and a central control unit or microprocessor operatively coupled to each of accelerometer, gyroscope, and the magnetometer.

Next, an illustrative manner in which the at least one data processing device of the head-mounted display system 100 performs the inertial measurement unit (IMU) calculations will be explained in detail. In particular, this calculation procedure will describe the manner in which the orientation and position of the head of the user could be determined using the signals from the inertial measurement unit (IMU) of the system 100. As explained above, in the illustrative embodiment, the inertial measurement unit may include the following three triaxial sensor devices: (i) a three-axis accelerometer sensing linear acceleration $\vec{\alpha}'$, (ii) a three-axis rate gyroscope sensing angular velocity $\vec{\omega}'$, and (iii) a three-axis magnetometer sensing the magnetic north vector $\vec{n}'$. The inertial measurement unit senses in the local (primed) frame of reference attached to the IMU itself. Because each of the sensor devices in the IMU is triaxial, the vectors $\vec{\alpha}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the orientation $\vec{\theta}(t)$ and position $\vec{R}(t)$ in the global, unprimed, inertial frame of reference. Initially, the calculation procedure begins with a known initial orientation $\vec{\theta}_0$ and position $\vec{R}_0$ in the global frame of reference.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement unit (IMU) provide calibrated data. In addition, all of the signals from the IMUs are treated as continuous functions of time. Although, it is to be understood the general form of the equations described herein may be readily discretized to account for IMU sensor devices that take discrete time samples from a bandwidth-limited continuous signal.

The orientation $\vec{\theta}(t)$ is obtained by single integration of the angular velocity as follows:

$$\vec{\theta}(t) = \vec{\theta}_0 + \int_0^t \vec{\omega}(t)dt \qquad (3)$$

$$\vec{\theta}(t) = \vec{\theta}_0 + \int_0^t \vec{\Theta}(t)\vec{\omega}'(t)dt \qquad (4)$$

where $\vec{\Theta}$ is the matrix of the rotation transformation that rotates the instantaneous local frame of reference into the global frame of reference.

The position is obtained by double integration of the linear acceleration in the global reference frame. The triaxial accelerometer of the IMU senses the acceleration $\vec{\alpha}'$ in the local reference frame. The acceleration $\vec{\alpha}'$ has the following contributors: (i) the acceleration due to translational motion, (ii) the acceleration of gravity, and (iii) the centrifugal, Coriolis and Euler acceleration due to rotational motion. All but the first contributor has to be removed as a part of the change of reference frames. The centrifugal and Euler accelerations are zero when the acceleration measurements are taken at the origin of the local reference frame. The first integration gives the linear velocity as follows:

$$\vec{v}(t) = \vec{v}_0 + \int_0^t \{\vec{a}(t) - \vec{g}\}dt \qquad (5)$$

$$\vec{v}(t) = \vec{v}_0 + \int_0^t \{\vec{\Theta}(t)[\vec{a}'(t) + 2\vec{\omega} \times \vec{v}'(t)] - \vec{g}\}dt \qquad (6)$$

where $2\vec{\omega}' \times \vec{v}'(t)$ is the Coriolis term, and where the local linear velocity is given by the following equation:

$$\vec{v}'(t) = \vec{\Theta}^{-1}(t)\vec{v}(t) \qquad (7)$$

The initial velocity $\vec{v}_0$ can be taken to be zero if the motion is being measured for short periods of time in relation to the duration of Earth's rotation. The second integration gives the position as follows:

$$\vec{R}(t) = \vec{R}_0 + \int_0^t \vec{v}(t)dt \qquad (8)$$

At the initial position, the IMU's local-to-global rotation's matrix has an initial value $\vec{\Theta}(0) \equiv \vec{\Theta}_0$. This value can be derived by knowing the local and global values of both the magnetic north vector and the acceleration of gravity. Those two vectors are usually non-parallel. This is the requirement for the $\vec{\Theta}_0(\vec{g}', \vec{n}', \vec{g}, \vec{n})$ to be unique. The knowledge of either of those vectors in isolation gives a family of non-unique solutions $\vec{\Theta}_0(\vec{g}', \vec{g})$ or $\Theta_0(\vec{n}', \vec{n})$ that are unconstrained in one component of rotation. The $\Theta_0(\vec{g}', \vec{n}', \vec{g}, \vec{n})$ has many implementations, with the common one being the Kabsch algorithm. As such, using the calculation procedure described above, the at least one data processing device of the system 100 may determine the orientation $\vec{\theta}(t)$ and position $\vec{R}(t)$ of one or more body portions of the user. For example, the orientation of the head of the user may be determined by computing the orientation $\vec{\theta}(t)$ and position $\vec{R}(t)$ of two points on the head of the user (i.e., at the respective locations of two inertial measurement units (IMUs) disposed on the head of the user).

In one or more alternative embodiments, rather than using an inertial measurement unit (IMU) that includes an accelerometer, a gyroscope, and a magnetometer, a single accelerometer may be used to simply measure the displacement of the head of the user (e.g., by using equation (8) described above). As explained above, the acceleration output from the accelerometer may be integrated twice in order to obtain the positional displacement of the head of the user.

Figure 19:
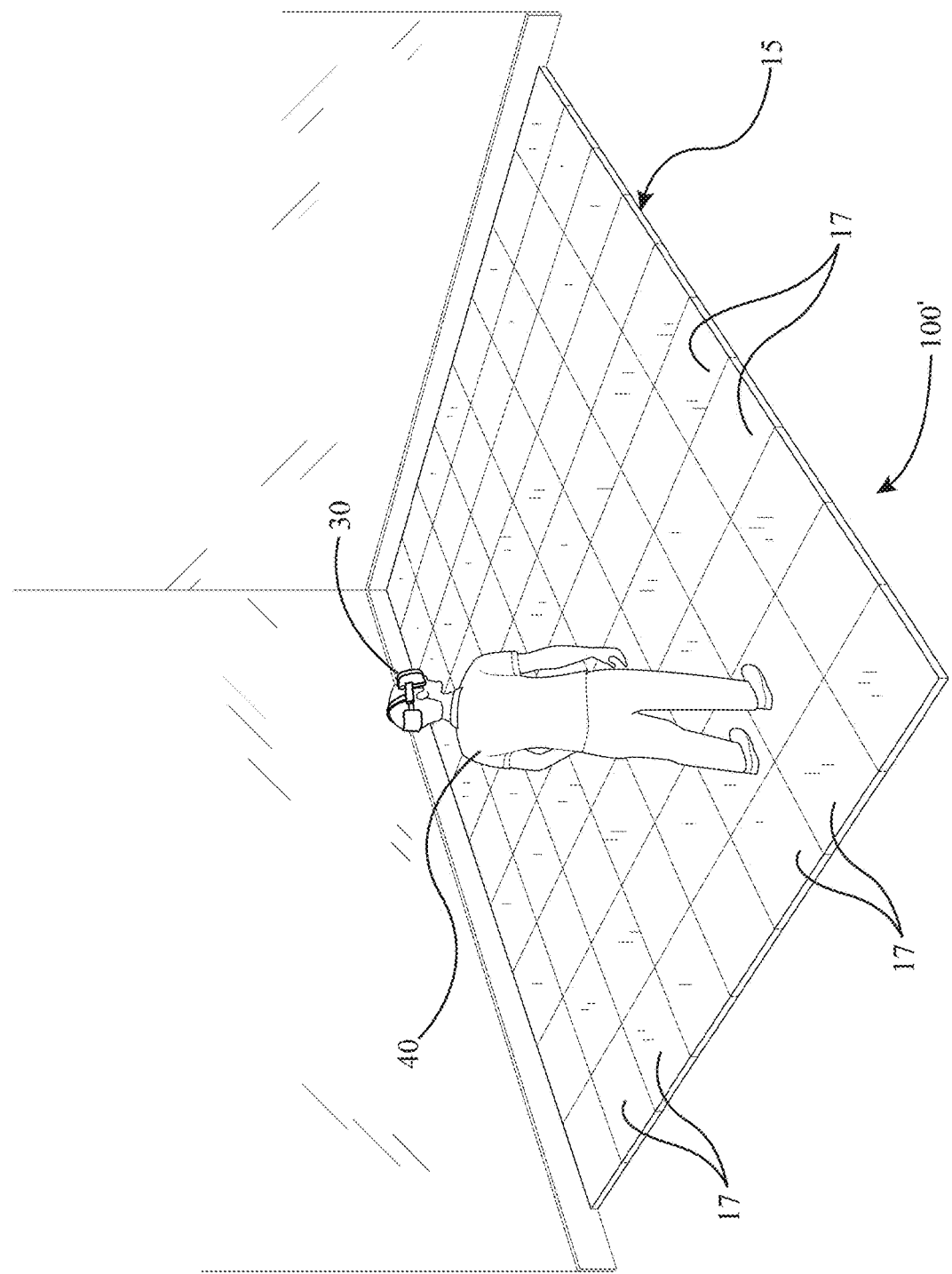
FIG. 19 is a perspective view of a head-mounted display system, according to another illustrative embodiment of the invention, wherein the head-mounted display system includes an instrumented floor together with the head-mounted visual display device.

In yet a further illustrative embodiment, with reference to FIG. 19, the head-mounted display system 100' further includes an instrumented floor 15. The instrumented floor 15 comprises a plurality of instrumented floor sections 17 that are configured to detect movements, forces, and/or moments for the user and generate one or more output signals based upon the detected movements, forces, and/or moments for the user. In this further illustrative embodiment, the at least one data processing device 20 is operatively coupled to the head-mounted visual display device 30 and the instrumented floor 15. The at least one data processing device 20 is programmed to receive the one or more output signals from the instrumented floor 15; and determine one or more movements, output forces, and/or output moments for the user based upon the one or more output signals from the instrumented floor 15. In this further illustrative embodiment, the instrumented floor 15 enables a plurality of different movement patterns and/or protocols to be executed by the user while the user is disposed on the instrumented floor 15.

With reference again to FIG. 19, in this further illustrative embodiment, the plurality of instrumented floor sections 17 may comprise a plurality of force measurement assemblies forming the instrumented floor 15. The plurality of force measurement assemblies are configured to detect forces and/or moments for the user and generate a plurality of output signals based upon the detected forces and/or moments for the user. In this further illustrative embodiment, the at least one data processing device 20 is further programmed to, in a first operational mode, determine the output forces and/or output moments separately for at least some of the plurality of force measurement assemblies forming the instrumented floor 15; and in a second operational mode, determine the output forces and/or output moments for individual ones of the plurality of force measurement assemblies, and then combine the output forces and/or output moments for at least some of the plurality of force measurement assemblies so as to form a virtual force measurement assembly. In the illustrative embodiment, the instrumented floor 15 comprises a plurality of force measurement assembly tiles 17 (i.e., force plate tiles 17) so that the user 40 is able to traverse the instrumented floor 15 while wearing the head-mounted visual display device 30 and interacting with the virtual reality environment or the augmented reality environment. In the illustrative embodiment, the instrumented floor 15 can have many different data channels (e.g., data channels for $F_x$, $F_y$, $F_z$, $M_x$, $M_y$, $M_z$, $CoP_x$, $CoP_y$). In the illustrative embodiment, the force channels can be separate to each force plate/floor tile 17 and/or the force channels can also be combined/fused to create virtual larger force tile(s). Because the instrumented floor 15 can be done with smaller instrumented tiles 17, the instrumented floor 15 can cover the space where the user is going to stand, walk, run, or do other activities on. Advantageously, the instrumented floor 15 may be configured to generate data points at much higher frequencies (e.g., within a 100 Hz-30,000 Hz frequency range) than video-based motion capture (MOCAP) systems (typically in the 30 Hz-300 Hz frequency range), which is very useful in movement analysis. Some applications are fall risk assessment, running starting time analysis, etc.

In this further illustrative embodiment, the at least one data processing device 20 is further programmed to determine the one or more output forces and/or output moments for the user from the plurality of output signals from the plurality of force measurement assemblies; and determine performance metrics for the user based upon the one or more output forces and/or output moments. In this further illustrative embodiment, the one or more performance metrics determined by the at least one data processing device 20 for the user are selected from a group consisting of: (i) a postural stability parameter, (ii) a center of pressure for the user, (iii) a center of gravity for the user, and (iv) combinations thereof. In the illustrative embodiment, the force data from the instrumented floor 15 can be used to characterize the kinetic (ground reaction forces) of the subject standing on the force tile(s) 17. One also can derive various metrics about the user/subject based on the force data. For example, one can assess the stability of the user, given certain visual cues (e.g. the user standing at the edge of a virtual cliff, on a virtual tight rope, etc.). As another example, the center of pressure (CoP) and thus the center of gravity (CoG) can be derived and used for the detection of modalities of user reactions to certain "virtual" events, such as falling, virtual object avoidance, etc.

In this further illustrative embodiment, the head position sensing device of the head-mounted visual display device 30 (e.g., the inertial measurement unit (IMU) disposed in the head-mounted visual display device 30) may be configured to detect at least one of head position, head movement, head orientation, head velocity, and head acceleration of the user, and the at least one data processing device may be further programmed to: (i) determine the one or more output forces and/or output moments for the user from the one or more output signals from the one or more force measurement assemblies of the instrumented floor 15; (ii) determine the at least one of the head position, the head movement, the head orientation, the head velocity, and the head acceleration of the user from the head position and/or movement sensing device; and (iii) assess balance and/or body stability for the user based upon both the one or more output forces and/or output moments from the one or more force measurement assemblies and the at least one of the head position, the head movement, the head orientation, the head velocity, and the head acceleration of the user from the head position and/or movement sensing device. In this further illustrative embodiment, the one or more output forces for the user may comprise the ground reaction force (GRF) for the user, which is the force the ground exerts on any object in contact with it, such as the human body during movements like walking, running, or jumping. The important aspects of the ground reaction force (GRF) include: (i) magnitude and direction, and (ii) GRF components. Considering magnitude and direction, the GRF varies in intensity depending on the activity, being higher in running than walking, for instance. The GRF direction is typically opposite to the applied force. Considering the GRF components, the GRF may be analyzed in three dimensions: (i) vertical (supporting body weight), (ii) anterior-posterior (forward and backward motion), and (iii) medial-lateral (side-to-side stability). In gait analysis, ground reaction force (GRF) plays a pivotal role. The GRF is used to study walking and running patterns, helping in rehabilitation, enhancing sports performance, and diagnosing movement disorders. Integrating GRF measurements from the instrumented floor 15 with data from the head position sensing device of the head-mounted visual display device 30 (e.g., the inertial measurement unit (IMU) disposed in the head-mounted visual display device 30) profoundly enriches gait analysis because this combination yields a comprehensive view of an individual's gait dynamics. The significance of this integration is twofold. First, the integration results in comprehensive gait dynamics where the force plates of the instrumented floor 15 provide precise GRF data including magnitude, direction, and application point during gait, essential for understanding body-ground interaction. The HMD-based head position sensing device complements the force plate data of the instrumented floor 15 by capturing head movements, orientation, and acceleration, crucial for balance and stability analysis. Secondly, the integration results in a comprehensive balance and stability analysis where the HMD-based head position sensing device monitors head movements, pivotal for balance, while the force plates of the instrumented floor 15 provide precise GRF data. Advantageously, analyzing head stability alongside GRF data allows for a thorough assessment of an individual's balance and body stabilization during motion, vital for pinpointing gait irregularities.

In this further illustrative embodiment, a plurality of different users and/or objects may be disposed on the instrumented floor 15, and the at least one data processing device 20 is further programmed to determine positions and/or movements for the plurality of different users and/or objects disposed on the instrumented floor 15 using the one or more output signals. In the illustrative embodiment, the instrumented floor 15 can also measure and keep track of multiple users/subjects and objects resting or moving on the instrumented floor 15. Due to the high sensitivity of the instrumented floor 15, minute perturbations can be measured for any object or user/subject on the instrument floor 15. Also, in the illustrative embodiment, the force data from the instrumented floor 15 can enhance the virtual video projected to the user. For example, the tapping of one's foot versus the stomping of one's foot on the instrumented floor 15 can be used to project virtual indentations on the virtual project ground/surface.

In this further illustrative embodiment, the at least one data processing device 20 is further programmed to generate at least one of visual feedback, auditory feedback, and/or tactile feedback for the user based upon the one or more output signals from the instrumented floor 15. The at least one data processing device 20 may be further programmed to generate the visual feedback for the user based upon the one or more output signals from the instrumented floor 15 by displaying one or more virtual objects to the user using the head-mounted visual display device 30. In this further illustrative embodiment, the instrumented floor 15 comprises one or more vibratory devices for providing the tactile feedback for the user, and the at least one data processing device 20 may be further programmed to generate the tactile feedback for the user based upon the one or more output signals from the instrumented floor 15 by generating one or more tactile sensations for the user using the one or more vibratory devices. In the illustrative embodiment, the force data for the instrumented floor 15 also can be used to generate acoustic feedback for the user.

The head-mounted display system 100' illustrated in FIG. 19 has many different applications. For example, the head-mounted display system 100' has various applications in (i) gait analysis and rehabilitation, (ii) sports training, (iii) virtual reality gaming, (iv) balance and posture training, (v) research, and (vi) architectural and design. Initially, for gait analysis and rehabilitation, the head-mounted display system 100' can be used for providing visual feedback (e.g., patients undergoing rehabilitation can receive real-time visual feedback on their gait pattern through the head-mounted visual display device 30, which can aid in self-correction). Also, for gait analysis and rehabilitation, the head-mounted display system 100' can be used for providing virtual scenarios. For example, the head-mounted display system 100' can create virtual terrains or obstacles that patients must navigate, challenging them and aiding in their recovery. Also, the instrumented floor 15 can provide data on how well the patients are adjusting their gait in different scenarios.

For sports training, the head-mounted display system 100' can be used for performance analysis (e.g., athletes can receive feedback on their footwork, balance, and force distribution as they train). Also, for sports training, the head-mounted display system 100' can be used for skill development (e.g., in-game situations can be simulated and the head-mounted display system 100' can provide athletes with real-time feedback on their biomechanics).

For virtual reality gaming, the head-mounted display system 100' can be used for creating immersive experiences. As a result of the instrumented floor 15 of the head-mounted display system 100', games can be designed where players must use their whole body, and the feedback from the floor 15 can be used to inform game mechanics, like jumping, running, or dodging. Also, for virtual reality gaming, the head-mounted display system 100' can be used for creating real-world effects (e.g., if a player is "hit" in a game, the floor could simulate the force, adding a tactile dimension to the gameplay).

For balance and posture training, the head-mounted display system 100' can be used for creating interactive scenarios. For example, users could be placed in virtual environments that challenge their balance, like a tightrope or shifting platform. The instrumented floor 15 provides data on how they adjust and maintain balance. Also, for balance and posture training, the head-mounted display system 100' can be used for biofeedback. For example, real-time data on weight distribution can be visualized in the head-mounted visual display device 30, helping users understand and correct their posture.

For research, the head-mounted display system 100' can be used for studying human biomechanics. For example, the head-mounted display system 100' can be used to study the intricacies of human movement in various scenarios, collecting data on how different visual stimuli affect movement and balance. Also, for research, the head-mounted display system 100' can be used for ergonomics assessments. For example, the head-mounted display system 100' can be used to test how people move and distribute their weight in various work settings or when interacting with different objects/tools.

For safety and evacuation training, the head-mounted display system 100' can be used for simulating scenarios. For example, the head-mounted display system 100' can be used to create virtual emergencies, like a building fire or ship sinking, and train individuals on how to evacuate safely. The instrumented floor 15 can provide data on the efficiency of movements, possible trip hazards, etc.

For entertainment and interactive exhibits, the head-mounted display system 100' can be used for creating immersive experiences. For example, the head-mounted display system 100' can be used by museums or theme parks to create interactive exhibits where visitors navigate virtual scenarios, with the floor capturing their reactions and movements.

For architecture and design, the head-mounted display system 100' can be used for simulating environments. For example, before building, architects and designers can use the head-mounted display system 100' to simulate spaces, observing how individuals navigate them. The data from the instrumented floor 15 can inform design adjustments to optimize flow and safety.

In this further illustrative embodiment, the at least one data processing device 20 is further programmed to determine locations for one or more objects or persons based upon the one or more output signals from the instrumented floor 15; and depict, using the head-mounted visual display device 30, the one or more objects or persons in a virtual reality environment or augmented reality environment based upon the locations determined from the one or more output signals from the instrumented floor 15. In the illustrative embodiment, if there is more than one subject or object on the instrumented floor 15, more accurate locations can be estimated and better projected in the simulated virtual reality (VR) environment. Similarly, better object localization can be done in augmented reality projects based on the CoP data from the instrumented floor 15.

In this further illustrative embodiment, the at least one data processing device 20 is further programmed to generate one or more virtual terrains, virtual obstacles, and/or virtual people on the output screen of the head-mounted visual display device 30 so that the user is able to interact with the one or more virtual terrains, virtual obstacles, and/or virtual people in a virtual reality environment; and determine a performance of the user in the virtual reality environment with the one or more virtual terrains, virtual obstacles, and/or virtual people based upon the one or more output signals from the instrumented floor 15.

In still a further illustrative embodiment, with reference again to FIG. 1, the at least one camera 31 (e.g., two (2) cameras 31) of the head-mounted visual display device 30 is used in a pass-through mode as a safety feature of the head-mounted visual display device 30. The at least one camera 31 of the head-mounted visual display device 30 enables the user to see one or more images of a real-world environment outside of the head-mounted visual display device 30. The at least one camera 31 is configured to capture the one or more images of the real-world environment outside of the head-mounted visual display device 30. In this further illustrative embodiment, the at least one data processing device 20 is programmed to generate augmented digital content; receive an input signal from the input device 34, 36 based upon an input response by the user; and, in response to the input signal from the input device 34, 36, display at least a portion of the one or more images of the real-world environment captured by the at least one camera 31 on the output screen of the head-mounted visual display device 30, and overlay the augmented digital content over the one or more images of the real-world environment so that the user is able to quickly check his or her surroundings without removing the head-mounted visual display device 30 from his or her head. In the illustrative embodiment, the pass-through mode, which is enabled by the external facing camera(s) 31 on the head-mounted visual display device 30, allows users to see the real-world through the lenses of the device 30, but with the augmented digital content overlaid on top of the real-world images. As such, the pass-through mode of the head-mounted visual display device 30 effectively bridges the gap between virtual reality (VR) and augmented reality (AR).

The pass-through mode of the head-mounted visual display device 30 has various benefits, such as improving the spatial awareness of the user and enhancing interactive gaming. For spatial awareness, the pass-through mode of the head-mounted visual display device 30 allows users to quickly check their surroundings without taking off the headset. The pass-through mode of the head-mounted visual display device 30 is especially useful in environments where users are walking around because the mode provides a safety "pass-through" to real-world visuals. For example, in the illustrative embodiment, if a patient is feeling dizzy or nauseous and needs to escape the virtual reality scene, they can do so by pressing "X" or "A" on the input device 34, 36 (e.g., hand controllers 34, 36). In the illustrative embodiment, the pass-through mode is a black-and-white or color live view of the surrounding environment. Also, in the illustrative embodiment, when the pass-through toggle is activated on one or more graphical user interfaces of the head-mounted visual display device 30, the head-mounted visual display device 30 enables the pass-through function which disables the virtual world and shows a user his or her surroundings so that the user can orient himself or herself. When the pass-through toggle clicked again, the head-mounted visual display device 30 will turn off the pass-through function and shows the virtual world.

In this further illustrative embodiment, the at least one data processing device 20 is further programmed to receive a defined area within the real-world environment from the user that establishes one or more boundaries of the real-world environment; and display the one or more boundaries of the real-world environment within a virtual reality environment or an augmented reality environment so as to prevent the user from colliding with one or more objects in the real-world environment. In the illustrative embodiment, when setting up a virtual reality (VR) system, users can define a play area (i.e., a boundary setting). The pass-through mode allows the user to see the real world set to these boundaries, ensuring he or she does not collide into real-world objects.

In this further embodiment, the at least one data processing device 20 is further programmed to manipulate the augmented digital content such that the augmented digital content interacts with one or more actual objects in the real-world environment. In an interactive gaming application, game elements may be overlaid onto the real-world. For example, the user is playing a game where his or her living room becomes the game board, and virtual characters interact with the actual furniture in the living room.

In this further embodiment, the at least one data processing device 20 is further programmed to overlay instructions or data over the one or more images of the real-world environment so that the user is able to receive guidance as to how to interact with the real-world environment. In an education and training application, augmented reality (AR) may be used to overlay instructions or data onto real-world objects. For example, a mechanic wearing the head-mounted visual display device 30 could see annotated instructions on how to repair an engine.

In this further embodiment, the at least one data processing device 20 is further programmed to capture one or more hand movements of the user in the real-world environment using the at least one camera 31; and enable the user to interact with one or more virtual elements using the one or more hand movements of the user captured from the real-world environment. That is, the cameras 31 of the head-mounted visual display device 30 can be used for hand tracking, allowing users to interact with virtual elements using natural hand movements.

In this further embodiment, the at least one data processing device 20 is further programmed to perform object recognition on the one or more images of the real-world environment captured by the at least one camera 31 so as to identify one or more real-world objects; and generate the augmented digital content based upon the one or more real-world objects identified in the real-world environment so as to provide a context-aware augmented reality experience. Object recognition can enable context-aware augmented reality (AR) experiences. For example, pointing the cameras 31 of the head-mounted visual display device 30 at a book might bring up reviews or a summary.

It is readily apparent that the illustrative head-mounted display system 100, 100' described above offers numerous advantages and benefits. For example, the head-mounted display system 100, 100' is very beneficial for assessing balance and mobility. As another example, the head-mounted display system 100, 100' is useful for enhancing the visual motor performance of individuals. As yet another example, the head-mounted display system 100, 100' may be used as part of the rehabilitation regime for an orthopedic and/or neurological injury.

While reference is made throughout this disclosure to, for example, "an illustrative embodiment", "one embodiment", or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A head-mounted display system, comprising:
   a head-mounted visual display device having an output screen, the head-mounted visual display device configured to display one or more screen images on the output screen so that the one or more screen images are viewable by a user;
   an instrumented floor, the instrumented floor comprising one or more instrumented floor sections, the one or more instrumented floor sections configured to detect movements, forces, and/or moments for the user and generate one or more output signals based upon the detected movements, forces, and/or moments for the user; and
   at least one data processing device, the at least one data processing device operatively coupled to the head-mounted visual display device and the instrumented floor, the at least one data processing device being programmed to:
   receive the one or more output signals from the instrumented floor; and
   determine one or more movements, output forces, and/or output moments for the user based upon the one or more output signals from the instrumented floor;
   wherein the instrumented floor enables a plurality of different movement patterns and/or protocols to be executed by the user while the user is disposed on the instrumented floor.

2. The head-mounted display system according to claim 1, wherein the one or more instrumented floor sections comprise one or more force measurement assemblies, the one or more force measurement assemblies configured to detect one or more forces and/or one or more moments for the user and generate the one or more output signals based upon the detected one or more forces and/or one or more moments for the user.

3. The head-mounted display system according to claim 2, wherein the one or more force measurement assemblies comprise a plurality of force measurement assemblies forming the instrumented floor, the one or more output signals comprise a plurality of output signals outputted by the plurality of force measurement assemblies, and the at least one data processing device is further programmed to:
   in a first operational mode, determine the output forces and/or output moments separately for at least some of the plurality of force measurement assemblies forming the instrumented floor; and
   in a second operational mode, determine the output forces and/or output moments for individual ones of the plurality of force measurement assemblies, and then combine the output forces and/or output moments for at least some of the plurality of force measurement assemblies so as to form a virtual force measurement assembly.

4. The head-mounted display system according to claim 2, wherein the at least one data processing device is further programmed to:
   determine the one or more output forces and/or output moments for the user from the one or more output signals from the one or more force measurement assemblies; and
   determine performance metrics for the user based upon the one or more output forces and/or output moments.

5. The head-mounted display system according to claim 2, wherein the head-mounted visual display device further comprises a head position and/or movement sensing device operatively coupled to the at least one data processing device, the head position and/or movement sensing device configured to detect at least one of head position, head movement, head orientation, head velocity, and head acceleration of the user, and the at least one data processing device is further programmed to:
  determine the one or more output forces and/or output moments for the user from the one or more output signals from the one or more force measurement assemblies;
  determine the at least one of the head position, the head movement, the head orientation, the head velocity, and the head acceleration of the user from the head position and/or movement sensing device; and
  assess balance and/or body stability for the user based upon both the one or more output forces and/or output moments from the one or more force measurement assemblies and the at least one of the head position, the head movement, the head orientation, the head velocity, and the head acceleration of the user from the head position and/or movement sensing device.

6. The head-mounted display system according to claim 1, wherein a plurality of different users and/or objects are disposed on the instrumented floor, and the at least one data processing device is further programmed to:
  determine positions and/or movements for the plurality of different users and/or objects disposed on the instrumented floor using the one or more output signals.

7. The head-mounted display system according to claim 1, wherein the at least one data processing device is further programmed to:
  generate at least one of visual feedback, auditory feedback, and/or tactile feedback for the user based upon the one or more output signals from the instrumented floor.

8. The head-mounted display system according to claim 7, wherein the at least one data processing device is further programmed to:
  generate the visual feedback for the user based upon the one or more output signals from the instrumented floor by displaying one or more virtual objects to the user using the head-mounted visual display device.

9. The head-mounted display system according to claim 7, wherein the instrumented floor comprises one or more vibratory devices for providing the tactile feedback for the user, and wherein the at least one data processing device is further programmed to:
  generate the tactile feedback for the user based upon the one or more output signals from the instrumented floor by generating one or more tactile sensations for the user using the one or more vibratory devices.

10. The head-mounted display system according to claim 1, wherein the at least one data processing device is further programmed to:
  determine locations for one or more objects or persons based upon the one or more output signals from the instrumented floor; and
  depict, using the head-mounted visual display device, the one or more objects or persons in a virtual reality environment or augmented reality environment based upon the locations determined from the one or more output signals from the instrumented floor.

11. The head-mounted display system according to claim 1, wherein the at least one data processing device is further programmed to:
  generate one or more virtual terrains, virtual obstacles, and/or virtual people on the output screen of the head-mounted visual display device so that the user is able to interact with the one or more virtual terrains, virtual obstacles, and/or virtual people in a virtual reality environment; and
  determine a performance of the user in the virtual reality environment with the one or more virtual terrains, virtual obstacles, and/or virtual people based upon the one or more output signals from the instrumented floor.

* * * * *